United States Patent
Johannaber et al.

(10) Patent No.: US 11,554,024 B2
(45) Date of Patent: Jan. 17, 2023

(54) IMPACT FORCE FEEDBACK DISPLAY SYSTEM

(71) Applicant: Zimmer, Inc., Warsaw, IN (US)

(72) Inventors: Kenneth D. Johannaber, Reno, NV (US); John Minck, Jr., Reno, NV (US); Rida Hariri, Reno, NV (US); Derek Dalbey, Reno, NV (US)

(73) Assignee: Zimmer, Inc., Warsaw, IN (US)

( * ) Notice: Subject to any disclaimer, the term of this patent is extended or adjusted under 35 U.S.C. 154(b) by 92 days.

(21) Appl. No.: 15/800,988

(22) Filed: Nov. 1, 2017

(65) Prior Publication Data

US 2018/0116821 A1    May 3, 2018

Related U.S. Application Data

(60) Provisional application No. 62/416,443, filed on Nov. 2, 2016, provisional application No. 62/463,975, filed
(Continued)

(51) Int. Cl.
*A61F 2/46*    (2006.01)
*A61B 17/92*    (2006.01)
(Continued)

(52) U.S. Cl.
CPC ............ *A61F 2/46* (2013.01); *A61B 17/1659* (2013.01); *A61B 17/1668* (2013.01);
(Continued)

(58) Field of Classification Search
CPC ........... A61F 2/46; A61F 2/4603; A61B 17/92
(Continued)

(56) References Cited

U.S. PATENT DOCUMENTS

| | | | | |
|---|---|---|---|---|
| 4,615,209 A | * | 10/1986 | Change, Jr. | G01N 3/30 73/12.09 |
| 5,025,655 A | * | 6/1991 | Umemura | G01N 3/30 73/12.09 |

(Continued)

FOREIGN PATENT DOCUMENTS

| | | |
|---|---|---|
| CN | 103735303 A | 4/2014 |
| CN | 110035716 A | 7/2019 |

(Continued)

OTHER PUBLICATIONS

"U.S. Appl. No. 15/800,915, Non Final Office Action dated Aug. 22, 2019", 14 pgs.

(Continued)

*Primary Examiner* — Si Ming Ku
(74) *Attorney, Agent, or Firm* — Schwegman Lundberg & Woessner, P.A.

(57) ABSTRACT

Systems and methods may display an indication of an impact force from a driving device. A method may include displaying the indication of the impact force with a light. The light may be located on the driving device, a component attached to the driving device, a user interface, or the like. Different colors may be used to indicate different impact forces. For example, a first light color may correspond to an impact force below a first threshold, a second light color may correspond to an impact force above a second threshold, and a third light color may correspond to an impact force between the thresholds. The impact force may be detected using a sensor, which may output a voltage to cause the illumination.

12 Claims, 12 Drawing Sheets

Related U.S. Application Data on Feb. 27, 2017, provisional application No. 62/510,985, filed on May 25, 2017.

(51) Int. Cl.
  *A61B 17/16* (2006.01)
  *A61B 17/00* (2006.01)
  *A61B 90/00* (2016.01)

(52) U.S. Cl.
  CPC .... *A61B 17/92* (2013.01); *A61B 2017/00128* (2013.01); *A61B 2017/922* (2013.01); *A61B 2090/064* (2016.02); *A61B 2090/065* (2016.02); *A61B 2090/0807* (2016.02); *A61F 2002/4681* (2013.01)

(58) Field of Classification Search
  USPC .......................................................... 606/99
  See application file for complete search history.

(56) References Cited

U.S. PATENT DOCUMENTS

| | | | | |
|---|---|---|---|---|
| 5,108,400 | A * | 4/1992 | Appel | B25D 9/02 |
| | | | | 173/91 |
| 7,300,432 | B2 | 11/2007 | Surma et al. | |
| 8,167,823 | B2 * | 5/2012 | Nycz | A61F 2/4609 |
| | | | | 600/587 |
| 8,393,409 | B2 | 3/2013 | Pedicini | |
| 8,695,726 | B2 | 4/2014 | Pedicini | |
| 9,414,940 | B2 | 8/2016 | Stein et al. | |
| 10,660,760 | B2 | 5/2020 | Johannaber et al. | |
| 10,792,162 | B2 | 10/2020 | Johannaber et al. | |
| 10,842,636 | B2 | 11/2020 | Johannaber et al. | |
| 11,234,825 | B2 | 2/2022 | Johannaber et al. | |
| 2002/0101232 | A1 | 8/2002 | Mendes et al. | |
| 2004/0243148 | A1 | 12/2004 | Wasielewski | |
| 2005/0010301 | A1 | 1/2005 | Disilvestro et al. | |
| 2005/0101962 | A1 | 5/2005 | Schwenke et al. | |
| 2006/0069447 | A1 | 3/2006 | Disilvestro et al. | |
| 2006/0271199 | A1 | 11/2006 | Johnson | |
| 2007/0005145 | A1 | 1/2007 | Banks et al. | |
| 2007/0149981 | A1 | 6/2007 | Bhattacharyya | |
| 2008/0065225 | A1 | 3/2008 | Wasielewski et al. | |
| 2008/0294258 | A1 | 11/2008 | Revie et al. | |
| 2010/0217156 | A1 | 8/2010 | Fisher et al. | |
| 2010/0331734 | A1 | 12/2010 | Stein | |
| 2010/0331737 | A1 | 12/2010 | Stein et al. | |
| 2010/0332152 | A1 | 12/2010 | Stein | |
| 2011/0093087 | A1 | 4/2011 | Mcmahon et al. | |
| 2011/0319755 | A1 | 12/2011 | Stein et al. | |
| 2012/0220430 | A1 * | 8/2012 | Bucar | A63B 69/32 |
| | | | | 482/84 |
| 2013/0090737 | A1 | 4/2013 | Flaherty et al. | |
| 2013/0197656 | A1 | 8/2013 | Conrad | |
| 2014/0249535 | A1 | 9/2014 | McCarthy et al. | |
| 2014/0330281 | A1 | 11/2014 | Aghazadeh | |
| 2015/0018718 | A1 | 1/2015 | Aghazadeh | |
| 2015/0196343 | A1 | 7/2015 | Donald et al. | |
| 2015/0282856 | A1 * | 10/2015 | Haiat | A61F 2/4609 |
| | | | | 606/100 |
| 2015/0289890 | A1 | 10/2015 | Chen et al. | |
| 2015/0297362 | A1 | 10/2015 | Singh et al. | |
| 2016/0029952 | A1 | 2/2016 | Hunter et al. | |
| 2017/0007330 | A1 | 1/2017 | Britton et al. | |
| 2018/0161168 | A1 | 6/2018 | Johannaber et al. | |
| 2020/0276023 | A1 | 9/2020 | Johannaber et al. | |
| 2020/0383796 | A1 | 12/2020 | Johannaber et al. | |
| 2021/0022874 | A1 | 1/2021 | Johannaber et al. | |

FOREIGN PATENT DOCUMENTS

| | | |
|---|---|---|
| CN | 110049748 A | 7/2019 |
| DE | 10342823 A1 | 4/2005 |
| DE | 102008005180 A1 | 11/2008 |
| EP | 2335651 | 6/2011 |
| EP | 3058865 | 8/2016 |
| WO | 2013117909 | 8/2013 |
| WO | WO-2014144107 A1 | 9/2014 |
| WO | WO-2018111429 A1 | 6/2018 |

OTHER PUBLICATIONS

"U.S. Appl. No. 15/800,915, Response filed Jul. 1, 2019 to Restriction Requirement dated May 2, 2019", 8 pgs.

"U.S. Appl. No. 15/800,915, Restriction Requirement dated May 2, 2019", 9 pgs.

"U.S. Appl. No. 15/800,932, Non Final Office Action dated Oct. 31, 2019", 20 pgs.

"U.S. Appl. No. 15/800,932, Response filed Oct. 8, 2019 to Restriction Requirement dated Aug. 8, 2019", 8 pgs.

"U.S. Appl. No. 15/800,932, Restriction Requirement dated Aug. 8, 2019", 8 pgs.

"U.S. Appl. No. 15/801,025, Non Final Office Action dated Aug. 22, 2019", 14 pgs.

"U.S. Appl. No. 15/801,025, Response filed Jun. 27, 2019 to Restriction Requirement dated May 1, 2019", 7 pgs.

"U.S. Appl. No. 15/801,025, Restriction Requirement dated May 1, 2019", 6 pgs.

"Australia Application Serial No. 2017354043, First Examination Report dated Jun. 27, 2019", 3 pgs.

"Australia Application Serial No. 2017354043, Response filed Jul. 23, 2019 First Examination Report dated Jun. 27, 2019", 8 pgs.

"International Application Serial No. PCT US2017 059565, International Search Report dated Feb. 26, 2018", 5 pgs.

"International Application Serial No. PCT US2017 059565, Written Opinion dated Feb. 26, 2018", 8 pgs.

"International Application Serial No. PCT US2017 059559, International Search Report dated Mar. 5, 2018", 5 pgs.

"International Application Serial No. PCT US2017 059559, Written Opinion dated Mar. 5, 2018", 9 pgs.

"International Application Serial No. PCT/US2017/059552, International Search Report dated Feb. 20, 2018", 4 pgs.

"International Application Serial No. PCT/US2017/059552, Written Opinion dated Feb. 20, 2018", 7 pgs.

"U.S. Appl. No. 15/800,915, Advisory Action dated Apr. 2, 2020", 4 pgs.

"U.S. Appl. No. 15/800,915, Response filed Mar. 19, 2020 to Final Office Action dated Jan. 24, 2020", 11 pgs.

"U.S. Appl. No. 15/800,932, Notice of Allowance dated Mar. 18, 2020", 11 pgs.

"U.S. Appl. No. 15/801,025, Response Filed Mar. 23, 2020 to Notice of Non-Responsive Amendment", 10 pgs.

"Australian Application Serial No. 2019264529, First Examination Report dated Mar. 17, 2020", 4 pgs.

"Canadian Application Serial No. 3,042,672, Response filed Mar. 20, 2020 to Office Action dated Nov. 21, 2019", 11 pgs.

"European Application Serial No. 17817939.6, Response to Communication pursuant to Rules 161(1) and 162 EPC filed Dec. 17, 2020", 23 pgs.

"U.S. Appl. No. 15/800,915, Response Filed Nov. 22, 2019 to Non-Final Office Action dated Aug. 22, 2019", 11 pgs.

"U.S. Appl. No. 15/801,025, Response Filed Nov. 21, 2019 to Non-Final Office Action dated Aug. 22, 2019", 13 pgs.

"Canadian Application Serial No. 3,042,672, Office Action dated Nov. 21, 2019", 3 pgs.

"European Application Serial No. 17817317.5, Response to Communication pursuant to Rules 161(1) and 162 EPC filed Jan. 2, 2020", 88 pgs.

"U.S. Appl. No. 15/800,915, Final Office Action dated Jan. 24, 2020", 19 pgs.

"U.S. Appl. No. 15/800,932, Response filed Jan. 31, 2020 to Non Final Office Action dated Oct. 31, 2019", 12 pgs.

"European Application Serial No. 17804724.7, Response to Communication pursuant to Rules 161(1) and 162 EPC filed Feb. 3, 2020", 10 pgs.

(56) References Cited

OTHER PUBLICATIONS

"U.S. Appl. No. 17/070,433, Preliminary Amendment filed Oct. 29, 2020", 7 pages.
"Chinese Application Serial No. 201780072439.7, Response filed Nov. 17, 2020 to Office Action dated Aug. 19, 2020", with English claims, 11 pages.
"Chinese Application Serial No. 201780076110.8, Office Action dated Oct. 30, 2020", with English translation, 19 pages.
"Canadian Application Serial No. 3,045,624, Office Action dated May 12, 2020", 5 pages.
"Australian Application Serial No. 2019264529, Response filed Jul. 30, 2020 to Subsequent Examiners Report dated Jul. 27, 2020", 12 pages.
"Australian Application Serial No. 2019264529, Subsequent Examiners Report dated Jul. 27, 2020", 2 pages.
"Australian Application Serial No. 2019264529, Response filed Jun. 30, 2020 to First Examination Report dated Mar. 17, 2020", 19 pages.
"U.S. Appl. No. 15/800,915, Notice of Allowance dated Jul. 13, 2020", 10 pages.
"U.S. Appl. No. 15/801,025, Notice of Allowance dated Jun. 2, 2020", 10 pages.
"U.S. Appl. No. 16/875,408, Preliminary Amendment filed Jun. 10, 2020", 7 pages.
"U.S. Appl. No. 15/800,915, Corrected Notice of Allowability dated Aug. 19, 2020", 2 pgs.
"U.S. Appl. No. 15/801,025, Corrected Notice of Allowability dated Aug. 13, 2020", 2 pgs.
"Canadian Application Serial No. 3,045,624, Response filed Sep. 10, 2020 to Office Action dated May 12, 2020", 13 pgs.
"Chinese Application Serial No. 201780072439.7, Office Action dated Aug. 19, 2020", (W/English Translation), 21 pgs.
"Chinese Application Serial No. 201780076110.8, Response filed Jan. 27, 2021 to Office Action dated Oct. 30, 2020", with English claims, 9 pages.
"European Application Serial No. 17804724.7, Communication Pursuant to Article 94(3) EPC dated Feb. 28, 2022", 4 pgs.

\* cited by examiner

IMPACT FORCE FEEDBACK DISPLAY SYSTEM

CLAIM OF PRIORITY

This application claims the benefit of U.S. Provisional Patent Application Ser. No. 62/416,443, filed on Nov. 2, 2016, and claims the benefit of U.S. Provisional Patent Application Ser. No. 62/463,975, filed on Feb. 27, 2017, and claims the benefit of U.S. Provisional Patent Application Ser. No. 62/510,985, filed on May 25, 2017, the benefit of priority of each of which is claimed hereby, and each of which are incorporated by reference herein in its entirety.

BACKGROUND

A driving or impaction device may be used during joint implantation surgery to drive an instrument into bone and prepare the bone to receive an implant. Chiseling, for example is used to remove hard bone around an implant site to allow for the soft bone to receive an implant. A broach may be used to remove bone so that an implant may be placed. While applying force with the driving device, a surgeon may cause bone fracture, implant damage, or procedure delay if there is an overimpacting of tools or implants. Some manual techniques use audible feedback, such as listening for a change in tone of a bone or a surgeon watching broach movement to visually estimate bone assessment as the broach is driven into bone.

These techniques are imprecise and may not be able to prevent damage to a bone or an implant. These techniques may also be inconvenient and often require stopping, assessing, and restarting a procedure.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1A:
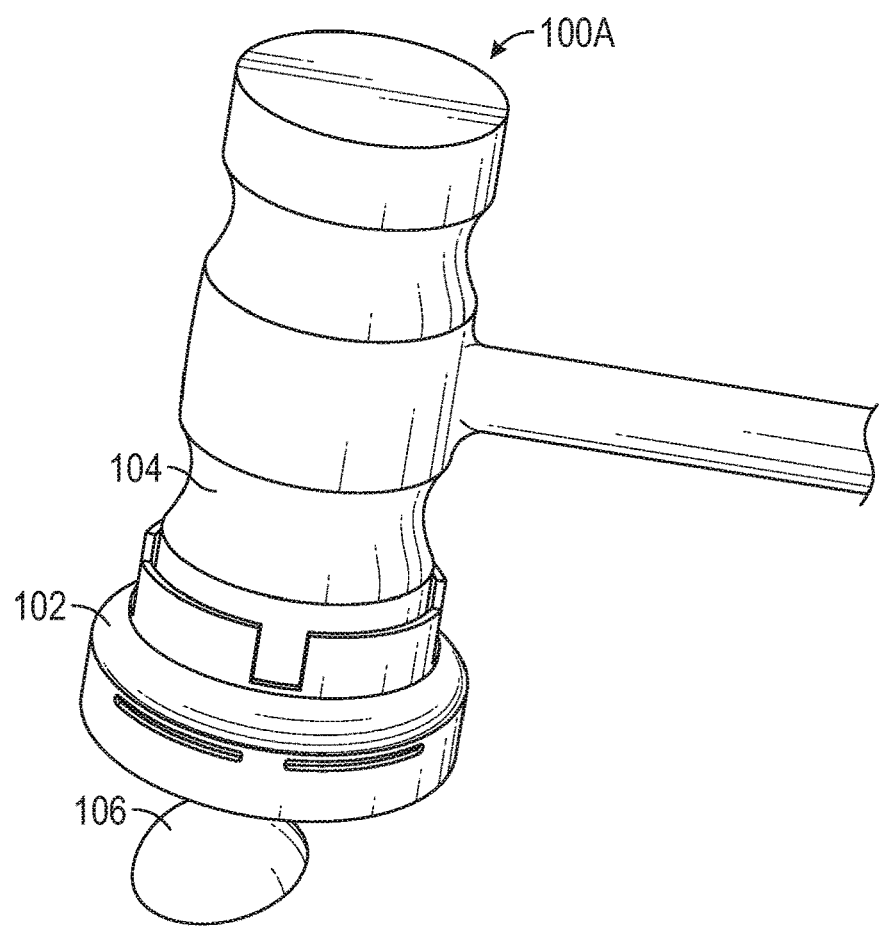
FIGS. 1A-1C illustrate a driving device, such as a surgical mallet, coupled to a striking component in accordance with some embodiments.

The present inventors recognized, among other things, that it would be beneficial to have a driving device capable of detecting the magnitude of an impaction force delivered by the device. Additionally, the present inventors have recognized that providing visual feedback regarding the magnitude of the delivered impact force may improve confidence for a surgeon using a driving device during a procedure. Providing visual feedback regarding the magnitude of the impact force may decrease adverse events, such as fatigue from repeated impacts due to low magnitude impacts or damage due to high magnitude impacts on implants, bones, or other structures that are struck by the impact. Presenting the visual feedback on the driving device allows a surgeon to focus on the task at hand, rather than needing to look away (e.g., at a display device or outside the surgical field), preventing the surgeon from losing concentration, and thus extending or delaying completion of the procedure.

The systems and techniques described herein include using a visual indication to present information related to an impact force imparted by a driving device. A driving device may include a mallet, a hammer, or other surgical device used to strike with force in a surgical field, such as to seat an implant during an orthopedic implant procedure.

A struck object may include a bone of a patient or an implant. When used to strike and seat an implant, a test object may also be used. The test object may be of a similar shape, size, or material to the implant to allow a surgeon to perform test strikes on the test object. The visual indication may be displayed on the driving device when striking the test object as if the test object were the implant.

The driving device may attach to a striking component or the driving device may include a light emitting diode (LED) or other lighting component to display information. For example, an array of colored LEDs may be used to display colored indications related to a striking or impact force. For example, a blue LED, set of LEDs, or lights may be used to correspond with an impact force that is of insufficient force to adequately perform a surgical procedure (e.g., below a threshold). In an example, a green LED, or set of LEDs, or light may correspond with an impact force that is within a range (e.g., between two thresholds). In an example, a red LED, or set of LEDs, or light may be used to indicate a force that is high enough (e.g., above a threshold) to potentially damage a struck object. Other colors may be used for a detected impact force. In an example, a threshold may be determined based on a patient-specific bone quality or a bone density determination.

In an example, other ranges or thresholds may be used. For example, a spectrum of LEDs may be used to display a continuous or a series of discrete colors that may progress as a detected impact force increases or decreases. For example, a minimum detected force may cause a base purple color LED to light up, and as the detected force increases with subsequent strikes, the color may change through a spectrum of indigo, blue, green, yellow, orange, red, etc., until a base red LED is lit corresponding with a maximum detected impact force. Any force detected above the maximum detected impact force may cause the base red LED to light up. Any force detected below the minimum detected force may cause the base purple color LED to light up or all LEDs may not light up or be prevented from lighting up, or white light may be emitted by an LED at the force below the minimum.

In an example, LEDs may light up for a predetermined period of time. For example, after an impact force is detected, an LED may light up for a second or a few seconds, or may stay lit until a subsequent impact force is detected or the lighting component of the driving device is deactivated. In another example, LEDs may blink, flash, pulsate (e.g., become brighter or dimmer), alternate colors, or otherwise change in response to a detected impact force. For example, an impact near a threshold may cause LEDs to light up, or alternate lighting up, with colors corresponding to impact forces above and below the threshold. For example, at a low threshold corresponding to a minimum force needed to seat an implant, if a force is detected near that minimum force, a blue LED and a green LED may alternate flashing, corresponding to a force below the minimum and above the minimum respectively. In another example, if an impact force is detected above a high threshold (e.g., corresponding to a force that may cause damage to a struck object, a bone, or an implant), a red LED may flash or blink to indicate danger.

The various combinations of light type, light color, and light display (e.g., flash, steady, pulsating, etc.), may be predetermined for the driving device or may be adjusted after manufacture. For example, brightness or dimness of the LEDs may be adjusted to the surgical field. These adjustments may be made by a surgeon or other user of the driving device, or may be changed automatically (e.g., a sensor may be used to determine an ambient brightness, and change the brightness of the LEDs in response).

In an example, impact thresholds may be adjusted, (e.g., by a surgeon), such as for use with different procedures, implants, bones, target objects, hammer sizes, etc. For example, impact thresholds (or ranges) may be adjusted when a procedure includes striking a bone versus an implant. In another example, impact thresholds may be adjusted based on a material (e.g., based on brittleness or hardness) of the implant.

A lighting component of a driving device maybe configured to display light in a line of sight of a user wielding the driving device. For example, the lighting component may be located on a striking surface or on an opposite side of the driving device from a striking surface. A user watching the driving device strike an object may see the lighting component naturally. The lighting component may be configured to be visible without requiring a change in function of the driving device. In other words, the lighting component may be visible to a surgeon using the driving device without the surgeon needing to change how the driving device is held or needing to change the striking motion used.

Figure 1B:
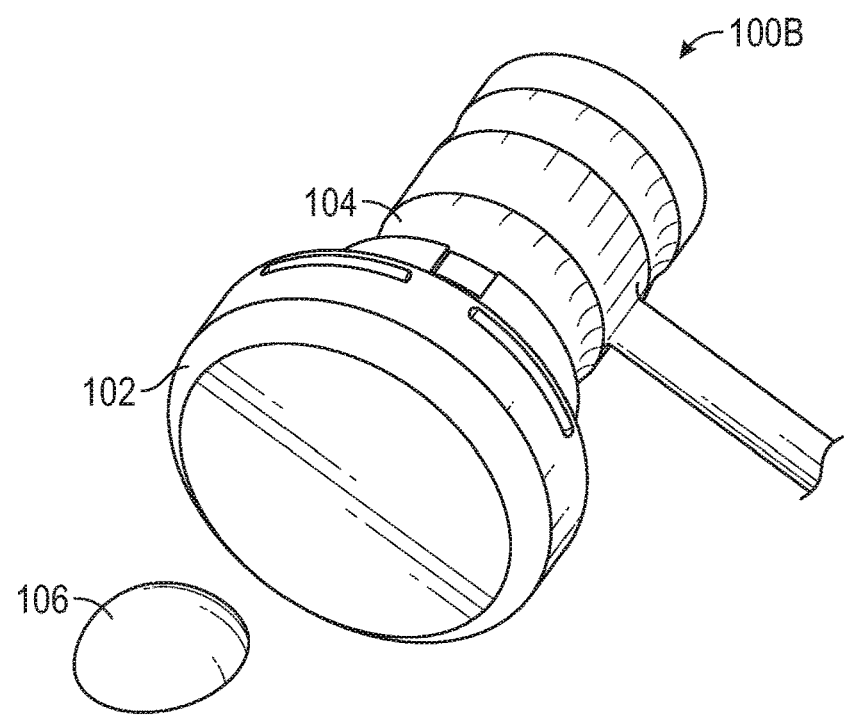
Figure 1C:
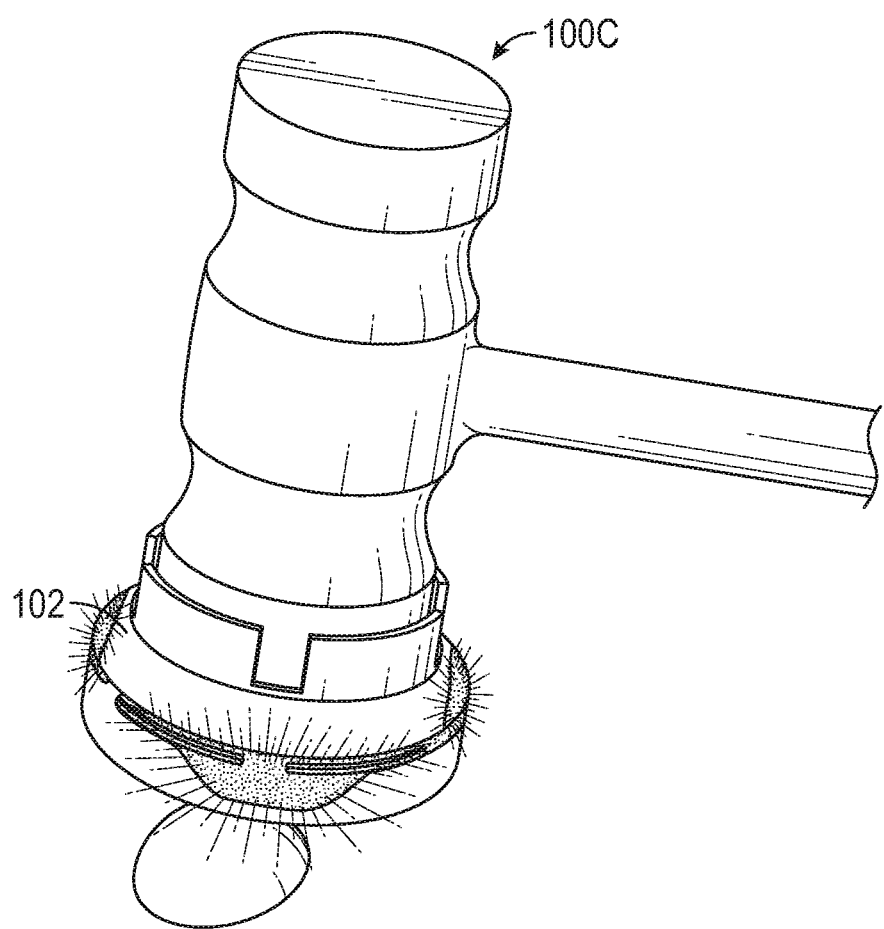

FIGS. 1A-1C illustrate a driving device 104, such as a surgical mallet, coupled to a striking component 102 in accordance with some embodiments. FIGS. 1A-1C illustrate a target object 106, which may simulate an implant or trial to be seated or struck by the driving device 104. The target object 106 may be struck to test the driving device 104 and the striking component 102, or to calibrate a surgeon's striking force. FIGS. 1A-1B illustrate two views 100A-100B of the driving device 104 coupled to the striking component 102 in proximity to the target object 106. In FIGS. 1A-1B, the striking component 102 is not lit up, indicating that no force is currently or was previously (e.g., within a timeframe, such as a few seconds) imparted on the striking component 102. In FIG. 1C, view 100C shows the striking component 102 lit up. The striking component 102 may be lit up using one or more light colors, patterns, or the like. For example, the striking component 102 may be lit with a first, second, or third color or pattern to indicate different forces.

The driving device 104 may be used to impart a force on an object in a surgical field. For example, driving device 104 may be held by a surgeon to cause the striking component 102 to come into contact with an object, such as an implant, a trial, or the target object 106. The striking component 102 may include a sensor, which may be used to determine a force imparted by the striking component 102 on the object (or the opposite force). After determining an impact force of the striking component 102 on the object, the striking component 102 may be used to display information corresponding to the impact force. For example, the striking component 102 may include a light, such as an LED, an array of lights, a display screen (e.g., a liquid crystal display (LCD) screen), or the like. The striking component 102 may include lights of differing colors or actions corresponding to different impact force profiles. For example, the impact force may be compared to a threshold or thresholds or a range or ranges to determine a corresponding profile that includes a display color or action. For example, when the impact force falls below a threshold, a first light or light pattern (e.g., a blue light, a slowly blinking light, etc.) may be used to indicate an insufficient force for an intended purpose (e.g., to seat an implant), such as by lighting up the striking component 102 as shown in view 100C of FIG. 1C. In another example, when the impact force may cause damage to the object, a second light or light pattern (e.g., a red light, a quickly flashing light, etc.) may be displayed using the striking component 102, such as by lighting up the striking component 102 as shown in view 100C of FIG. 1C. In yet another example, when the impact force is within a predetermined range, a third light or light pattern (e.g., a green light, a steady light, or etc.) may be displayed using the striking component 102 to indicate an accurate force, such as by lighting up the striking component 102 as shown in view 100C of FIG. 1C.

For certain uses of the driving device 104, multiple impacts may need to be performed before completion of a task. For each impact, the striking component 102 may show a light or pattern of lights corresponding to a force of the respective impact. For example, if a first impact force is too low for the particular purpose, the first light or light pattern may be shown to indicate to a user of the driving device 104 that a next impact should have a higher force. When the next impact is too high and potentially damaging, the second light or light pattern may be shown to indicate that the force should be decreased for subsequent strikes. When the next strike is within an acceptable range, the third light or light pattern may be shown to indicate that the force was appropriate and a similar force should be applied in future strikes. In this way, the user may fine tune strikes using the driving device 104 and feedback from the striking component 102 to determine and maintain an acceptable force. In an example, cumulative force or number of strikes may be tracked and displayed (e.g., displaying a light corresponding to a cumulatively tracked force, flashing a number of times to indicate a number of strikes, or increasing intensity or luminosity of light emitted by the striking component 102). For example, a displayed light may increase in intensity or change color in response to the cumulative force or number of strikes. The cumulative information may be used to provide a surgeon an indication of difficulty for a current impaction or a next strike.

Additional precision may be applied to the driving device 104 and the striking component 102, such as by using brightness, flashing lights, a display screen including a sensor reading or a proxy of a sensor reading (e.g., a number from 1 to 10, with 1 being a low force, and 10 being a high force, or 1 to 100, etc.), a series of lights, or the like. In an example, the striking component 102 may be a puck, which may couple with the driving device 104. For example, the puck may be affixed to the driving device 104. The puck may include an impaction surface, such as a thin film (e.g., around 2 in diameter), to measure the impaction. The thin film may be affixed around or to a surface of the striking component 102. The thin film may be a piezoelectric film, polymer, or other material that produces a voltage proportional to a force or strain induced in the film or material.

Figure 2:
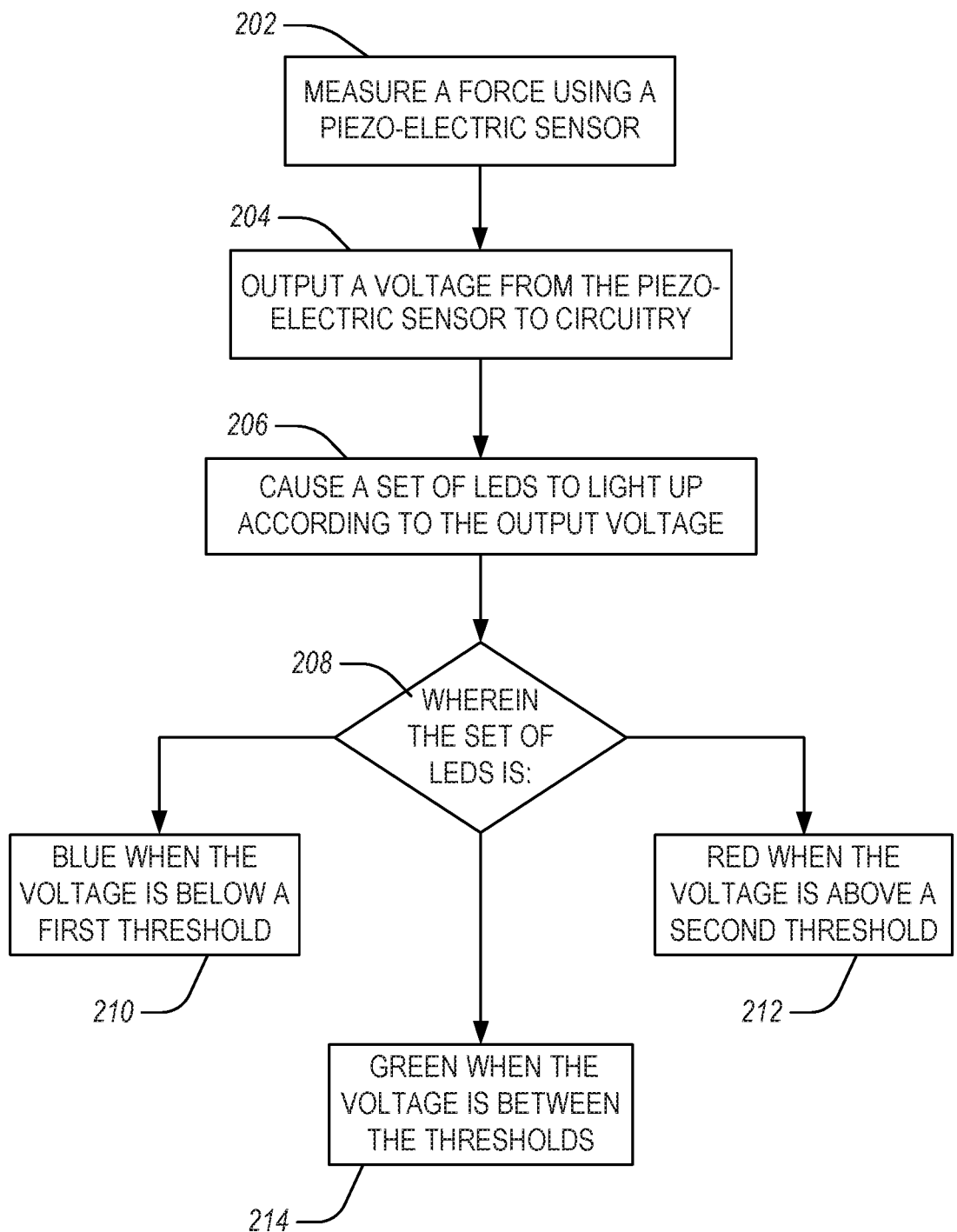
FIG. 2 illustrates a flow chart showing a technique for presenting visual feedback, such as an indication of an impact force, at a driving device in accordance with some embodiments.

FIG. 2 illustrates a flow chart showing a technique 200 for presenting visual feedback, such as an indication of an impact force, at a driving device in accordance with some embodiments. In an example, the driving device may be a surgical mallet. The surgical mallet may strike an implant to seat the implant. The technique 200 includes an operation 202 to measure an impact force using a piezo-electric sensor (or similar force sensor). The technique 200 includes an operation 204 to output a voltage from the piezo-electric sensor to a circuit. The technique 200 includes an operation 206 to cause, using the circuitry, a light, such as one or more LEDs or a set of LEDs to light up and display a first visual indication of the impact force based on the output voltage by illuminating at least a portion of the striking component. In an example, the output voltage may correspond to the impact force.

The technique 200 includes a decision operation 208 to determine a state of the output voltage relative to one or more thresholds. The technique 200 includes an operation 210 to, in response to determining that the voltage is below a first threshold, cause the set of LEDs to illuminate at least one blue LED. The technique 200 includes an operation 212 to, in response to determining that the voltage is above a second threshold, cause the set of LEDs to illuminate at least one red LED. The technique 200 includes an operation 214 to, in response to determining that the voltage is between the first threshold and the second threshold, cause the set of LEDs to illuminate at least one green LED. Other color combinations may be used without deviating from the scope of this disclosure. In another example, the technique 200 can include determining whether the output voltage falls within a plurality of ranges, where each of the ranges of voltage can control different LED operations.

The technique 200 may include using the color of the light to indicate information to a surgeon. For example, the red color light may indicate potential damage to an implant and the blue color light may indicate an insufficient force to seat the implant. In an example, the first and second thresholds are predetermined. In an example, the impact force is exerted by the striking component on a target object, the target object including one of a bone of a patient, an implant, a trial, or a test object. The technique 200 may include causing the striking component to be detached from the driving device. In an example, the technique 200 may include detecting the impact force using a force ring within the striking component that is compressed by the impact force to determine the impact force. In another example, the technique 200 may include detecting the impact force using a piezo-electric sensor within the striking component to determine the impact force. The driving device may be a surgical mallet.

Figure 3:
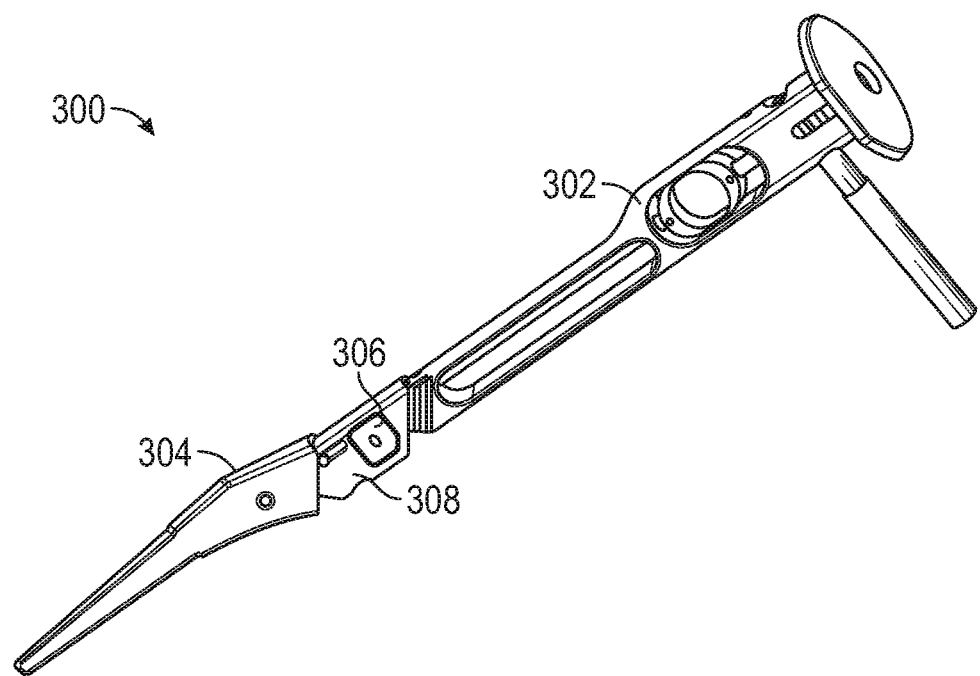
FIG. 3 illustrates a broaching device in accordance with some embodiments.

FIG. 3 illustrates a broaching device 300 in accordance with some embodiments. The broaching device 300 includes a driver handle 302, a broach 304, a sensor adapter 308, and a sensor unit 306. In an example, the broach 304 is removable, disposable, or patient-specific. The sensor unit 306 may include an accelerometer, pressure sensor, microphone, ultrasonic transceiver, a piezoelectric sensor, a resistive force sensor, a capacitive force sensor, or other force sensor. The sensor unit 306 may include circuitry or electronic components to power a sensor, read sensor data, collect data from the sensor, transmit data, or the like. The sensor adapter 308 may be removably coupled to the driver handle 302 or may be integrated into the driver handle 302.

In an example, the driver handle 302 is used to drive the broach 304 into an implant or a bone. The sensor unit 306 detects a force exerted by the driver handle 302 to drive the broach 304 into the implant or the bone. In an example, the sensor unit 306 may be incorporated into the driver handle 302 such that the sensor unit 306 may be used with multiple different broaches without any change to the sensor unit 306 or without needing to recalibrate the sensor unit 306. In an example, the driver handle 302 may be used for chiseling or broaching. In another example, the driver handle 302 may be used for setting a final implant (e.g., a permanent implant). The sensor unit 306 may be used to set the final implant, such as without changing the sensor unit 306.

In an example, a surgeon may watch for broach movement, and if there is no movement, increase force exerted using the broaching device 300. If the broach does not move when the surgeon closes in on a maximum force, feedback may be provided to the surgeon indicating that the broach may have an issue. The feedback may suggest that the broach be removed and examined.

The techniques discussed above in reference to the impact driver (FIGS. 1A-2) can be similarly applied to the broaching device 300. The sensor unit 306, sensor adapter 308 and/or driver handle 302 can include similar circuity and LED lighting to provide similar feedback to a surgeon utilizing the boarding device 300.

Figure 4:
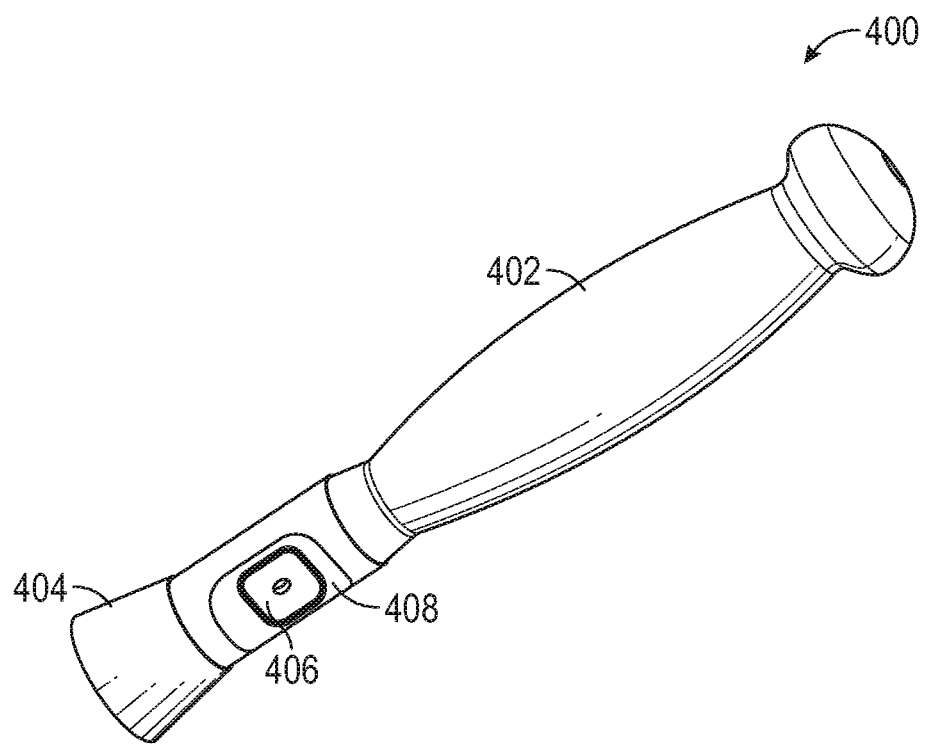
FIG. 4 illustrates a ball driver device in accordance with some embodiments.

FIG. 4 illustrates a ball driver device 400 in accordance with some embodiments. The ball driver device 400 includes a driver handle 402, a ball puck 404, a sensor unit 406, and a sensor adapter 408. In an example, the ball puck 404 is removable, disposable, or patient-specific. The sensor unit 406 may include an accelerometer, pressure sensor, microphone, ultrasonic transceiver, a piezoelectric sensor, a resistive force sensor, a capacitive force sensor, or other force sensor. The sensor adapter 408 may be removably coupled to the driver handle 402 or may be integrated into the driver handle 402.

In an example, the driver handle 402 is used to drive the ball puck 404 into an implant or a bone. In an example, the sensor unit 406 may be embedded in the driver handle 402.

The sensor unit 406 may continue to be used when the ball puck 404 is removed or replaced, such as without recalibrating the sensor unit 406. The sensor unit 406 may include circuitry or electronic components to power a sensor, read sensor data, collect data from the sensor, transmit data, or the like.

In an example, when the ball puck 404 is placed at the end of a trunnion, such as to replace a hip ball with ceramic or steel ball, there may be damage to the implant ball when it is struck. The ball driver device 400 may be used to show an impact force. In an example, a surgeon may calibrate a ceramic ball by using the ball driver device 400 to determine a force that would cause the ceramic ball to crack. This calibration may be performed by the surgeon or prior to use, such as when manufactured or assembled. In an example, the crack force may be communicated to the surgeon. In an example, a predetermined minimum force to allow the impact to be effective in placing the ball may be used. In an example, a maximum force such that the ball does not break may be used. Feedback may be provided to a surgeon to identify whether a force applied falls between the minimum and the maximum or outside that range.

In an example, measurements may be taken of an initial number of impacts by the ball driver device 400. An alert may be issued to the surgeon to reduce an applied force if the force exceeds a maximum or an initial maximum force (e.g., an initial force, that when increased may exceed a final maximum force). In another example, the alert may indicate that the surgeon may increase a force by a specified increment or a threshold may be indicated to the surgeon.

The broaching device 300 or the ball driver device 400, as described above, may provide a reduction of risk for fracture of a bone from cortical impact. The devices 300 or 400 may provide a reduction of risk of fretting (e.g., false-brinelling) of ball to neck insertion. In an example, an increase in positive feedback may be provided during broaching with the broaching device 300 to ensure a broach is moving during each mallet strike on the driver. In an example, a surgeon may use the broaching device 300 instead of listening for tone changes during implant or tooling driving processes.

In an example, the sensor unit 306 or the sensor unit 406 enables viewing and collection of data to establish patient-specific surgical techniques and postoperative care. Data output may include quantitative assessment of techniques that represent an improvement over surgeon skill-level-determined results. In an example, if postoperative risk is determined to be high (e.g., due to detected high force applied on a bone or implant), postoperative guidance may include longer recovery or limited activity requirements. In an example, applied force data may be used to establish a standard for driver impact values used in a variety of joint replacement procedures.

In an example, a sensor of the sensor unit 306 or the sensor unit 406 (e.g., an accelerometer, a piezoelectric sensor, a resistive force sensor, a capacitive force sensor, etc.) may be positioned such that the axis of acceleration of the sensor is in-line with the impact vector of the broaching device 300 or the ball driver device 400. The sensing unit 306 or the sensor unit 406 may output a voltage proportional to a size acceleration that the driving device or implant experiences with each strike. A sensor of the sensing unit 306 or the sensor unit 406 may be calibrated to output the voltage as a function of the force the broaching device 300, the ball driver device 400, or implant encounters. In an example, an oscilloscope may be used to test and find optimum forces. The oscilloscope may be used to calibrate the broaching device 300, the ball driver device, or a sensor of the sensing unit 306 or the sensor unit 406, such as at the manufacturer or assembler. In an example, a surgeon may not need to calibrate the driving device or sensor if it is previously calibrated.

As with the broaching device 300, the techniques discussed above in reference to the impact driver (FIGS. 1A-2) can be similarly applied to the ball driver device 400. The sensor unit 406, sensor adapter 408 and/or driver handle 402 can include similar circuitry and LED lighting to provide similar feedback to a surgeon utilizing the ball driver device 400.

Figure 5:
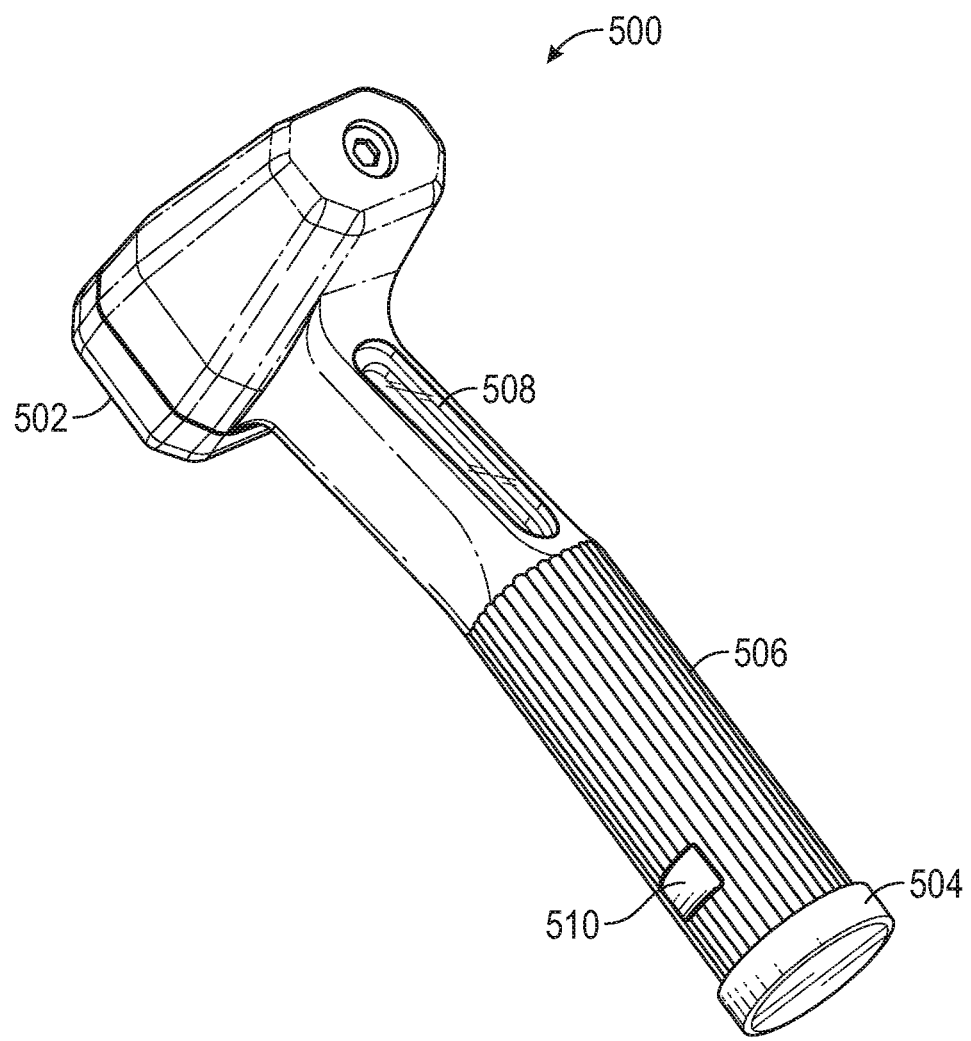
FIG. 5 illustrates a driving device, such as a surgical mallet, including a display portion in accordance with some embodiments.

FIG. 5 illustrates a driving device 500, such as a surgical mallet, including a display component 508 in accordance with some embodiments. The driving device 500 includes a striking component 502 and a graspable handle component 506. The driving device 500 may include a locking mechanism 510 for a removable component 504. In an example, the display component 508 is integrated into the graspable handle component 506. In another example, the display component 508 is integrated into the removable component 504. In yet another example, the display component 508 may be separately removable, and may snap into place or otherwise be held in compression within a housing of the driving device 500. The graspable handle component 506 may be hollow, into which the removable component 504 may be inserted. The graspable handle component 506 may include a shaft including a force sensor or the display component 508. In an example, a force sensor and the display component 508 may be located on or within a removable component, and the striking component 502 may be a stock instrument (e.g., without specialized components for detecting or display the forces).

The driving device 500 may be used to impart a force on an object in a surgical field. For example, the graspable handle 506 may be held by a surgeon to cause the striking component 502 to come into contact with an object. A sensor in the driving device 500, such as within the striking component 502, may be used to determine a force imparted by the striking component 502 on the object (or the opposite force). After determining an impact force of the striking component 502 on the object, the display component 508 may be used to display information corresponding to the impact force. For example, the display component 508 may include a light, such as an LED, an array of lights, a display screen (e.g., a liquid crystal display (LCD) screen), or the like. The display component 508 may include lights of differing colors or actions corresponding to different impact force profiles. For example, the impact force may be compared to a threshold or thresholds or a range or ranges to determine a corresponding profile that includes a display color or action. For example, when the impact force may cause damage to the object, a red light may be displayed using the display component 508. In another example, when the impact force is within a predetermined range, a green light may be displayed using the display component 508 to indicate an accurate force. In yet another example, when the impact force falls below a threshold, a blue or yellow light may be used to indicate an insufficient force for an intended purpose (e.g., to seat an implant).

For certain uses of the driving device 500, multiple impacts may need to be performed before completion of a task. For each impact, the display component 508 may show a light or pattern of lights corresponding to a force of the respective impact. For example, if a first impact force is too low for the particular purpose, a blue light may be shown to indicate to a user of the driving device 500 that a next impact should have a higher force. When the next impact is too high and potentially damaging, a red light may be shown to indicate that the force should be decreased for subsequent strikes. When the next strike is within an acceptable range, a green light may be shown to indicate that the force was appropriate and a similar force should be applied in future strikes. In this way, the user may fine tune strikes using the driving device 500 and feedback from the display component 508 to determine and maintain an acceptable force. In an example, cumulative force or number of strikes may be tracked and displayed (e.g., displaying a light corresponding to a cumulatively tracked force). For example, a displayed light may increase in intensity or change color in response to the cumulative force or number of strikes. The cumulative information may be used to provide a surgeon an indication of difficulty for a current impaction or a next strike.

Additional precision may be applied to the driving device 500 and the display component 508, such as by using brightness, flashing lights, a display screen including a sensor reading or a proxy of a sensor reading (e.g., a number from 1 to 10, with 1 being a low force, and 10 being a high force, or 1 to 100, etc.), a series of lights, or the like.

The driving device 500 may include a housing or component to allow for the locking mechanism 510 to lock the removable component 504 to the driving device 500. For example, the graspable handle component 506 may include a hole to receive the locking mechanism 510 when the removable component 504 is inserted into the driving device 500. In an example, the locking mechanism 510 maybe released by pressing the locking mechanism 510 and pulling the removable component 504 from the driving device 500.

Figure 6:
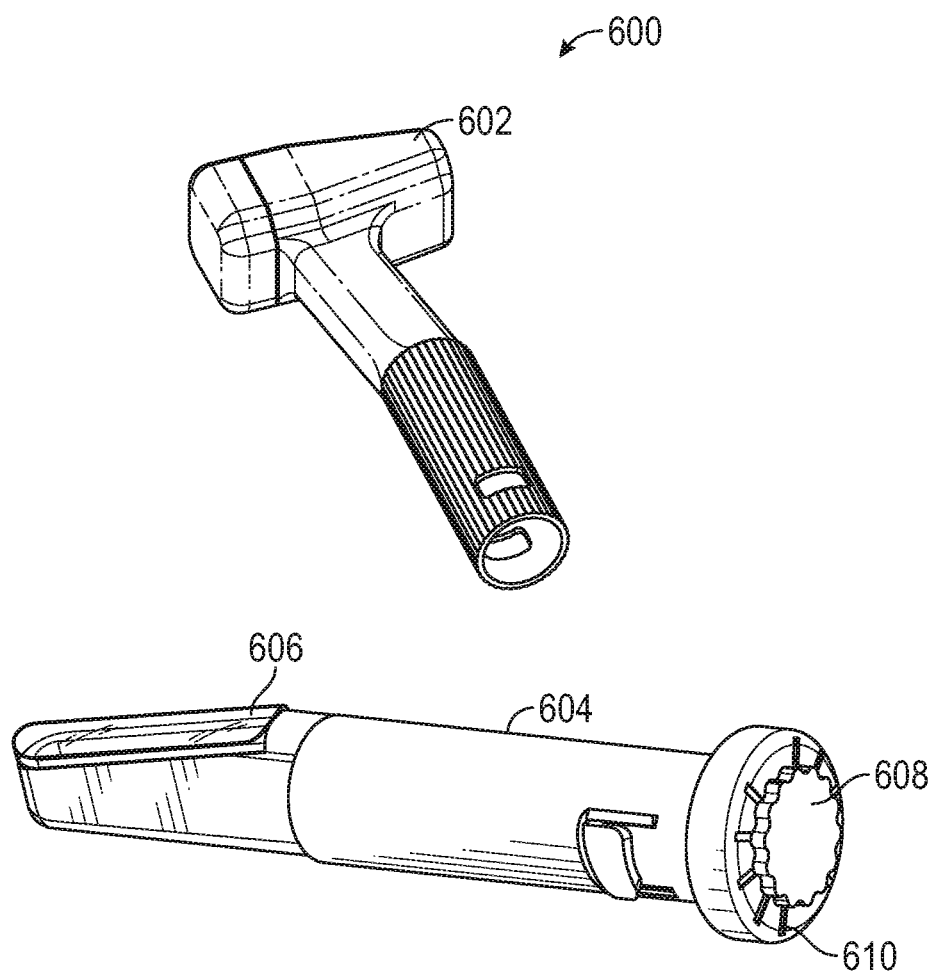
FIG. 6 illustrates a driving device system including a striking component and a removable component in accordance with some embodiments.

FIG. 6 illustrates a driving device system 600 including a striking component 602 and a removable component 604 in accordance with some embodiments. The removable component 604 includes a display component 606. The removable component 604 may include a selection mechanism 608, such as a rotational knob, a push button, a switch, other selectable physical toggle devices, or the like. In an example, the selection mechanism 608 may be used to activate or deactivate the display component 606. In an example, the selection mechanism 608 may be used to adjust a force range along a series of selectable options 610, which may include activating or deactivating the display component 606. For example, the selectable options 610 may include an off option, and an intensity settings. The intensity settings may be used to adjust brightness of the display component 606, change ranges or thresholds used to control display corresponding to detected impact forces, or the like.

The selectable options 610 may be used to toggle modes of the display component 606. For example, a first mode may include basic operation, such as predetermined thresholds and single light display. Other modes may include additional functionality, such as blinking, flashing, pulsing, etc., of lights in the display component 606, adjustable thresholds or ranges of forces, cumulative force tracking and display (e.g., displaying a light corresponding to a cumulatively tracked force, such as by increasing intensity or changing color of the light in response to the cumulative force), or the like. The modes may be preprogrammed or may be adjustable.

In an example, the selectable options 610 may be used to select different procedures or select between portions of a single procedure, which may automatically adjust settings throughout the driving device system 600. For example, selections may be made between different parts of a total hip arthroplasty procedure, such as where impaction may be used to seat a femoral head implant (e.g., a first portion of the procedure) and an acetabular cup implant (e.g., a second portion of the procedure). The selectable options 610 may include an option for seating the femoral head implant and an option for the acetabular cup implant. The selectable options 610 may be used to automatically adjust thresholds for different procedures or parts of procedures.

Figure 7:
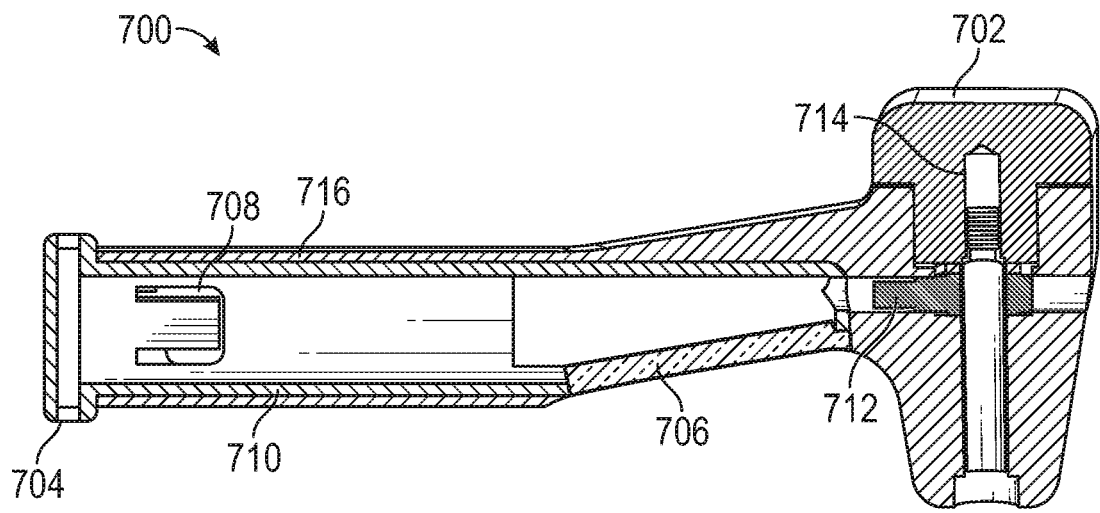
FIG. 7 illustrates a cross section of a driving device in accordance with some embodiments.

FIG. 7 illustrates a cross section of a driving device 700 in accordance with some embodiments. The driving device 700 includes a striking component 702, a removable component 704, and a display component 706. The display component 706 may be separate from, or integrated with, the removable component 704, the striking component, or a handle component 716.

The driving device 700 may include a locking mechanism 708. The locking mechanism 708 may be used to secure the removable component 704 to the driving device 700 or release the removable component 704 from the driving device 700. The locking mechanism 708 may engage with the handle component 716 of the driving device to lock the removable component 704 to the driving device 700.

In an example, the removable component 704 may include a battery housing 710. In another example, the handle component 716 may include the battery housing 710. A battery may be inserted in the battery housing 710. The battery may be used to power the display component 706, a sensor (e.g., sensor 712), or other components of the driving device 700 (e.g., a processor). A controller of the removable component 704 may be used to connect or disconnect the battery.

The driving device 700 may include a sensor 712, such as a force ring. The sensor 712 may be used to determine an impact force on the striking component 702. For example, the sensor 712 may be compressed in response to the impact force and the compression may be measured by the sensor 712 to determine the impact force. The impact force determined by the sensor 712 may be used to control the display component 706 as described above. In an example, the driving device 700 may include a connector 714, such as a coax connector. The connector 714 may be used to couple the sensor 712 to the striking component 702. In an example, the connector 714 may be used to secure the removable component 704 or the display component 706 to the driving device 700.

Figure 8A:
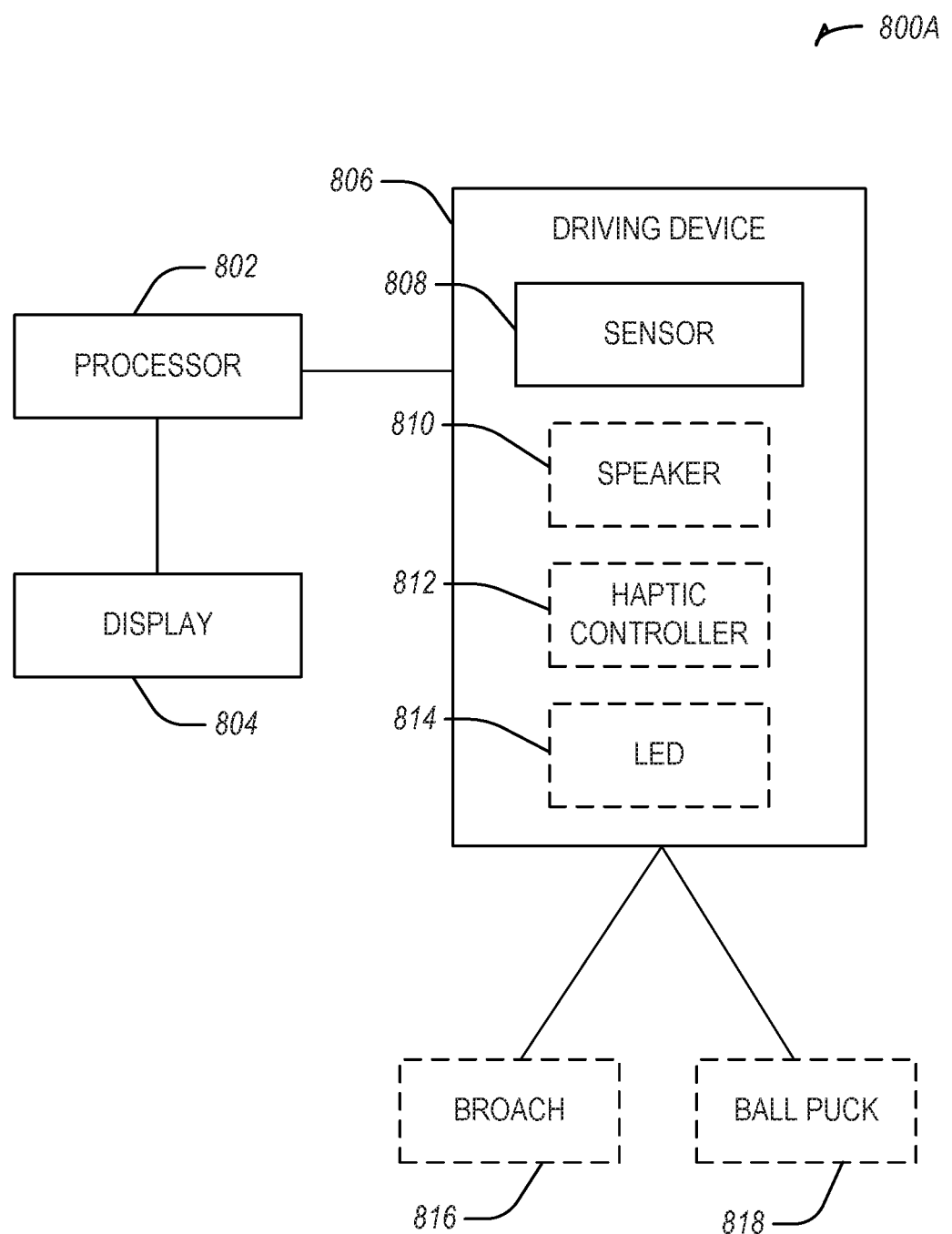
FIG. 8A illustrates an example system for preventing damage to an implant component, a bone, or soft tissue during surgery in accordance with some embodiments.

FIG. 8A illustrates a system 800A for preventing damage to an implant component, a bone, or soft tissue during surgery in accordance with some embodiments. The system may include a processor 802 coupled to a display 804. In an example, the processor 802 is in communication with a driving device 806A. In another example, the processor 802 is embedded in the driving device 806A. The driving device 806A includes a sensor 808, such as an accelerometer, pressure sensor, microphone, ultrasonic transceiver, a piezoelectric sensor, a resistive force sensor, a capacitive force sensor, or other force sensor (e.g., an accelerometer connected to a distal end of the driving device 806A). The driving device 806A may include a speaker 810, such as to provide an audible alert, a haptic controller 812, such as to provide haptic feedback, or a light emitting diode (LED) 814, such as to provide a visual alert. In an example, the driving device 806A may be coupled to a broach 816 or a ball puck 818. In another example, the broach 816 or the ball puck 818 may be incorporated into the driving device 806A. In an example, the driving device 806A may include a transceiver to wirelessly connect with the display 804. The display 804 may provide a visual alert corresponding to feedback.

In an example, the driving device 806A is used to apply force, such as a force on or using the broach 816 or the ball puck 818 to strike a bone. The applied force may include a broaching force, a rasping force, a chiseling force, or a seating force. The sensor 808 may detect an impact force, such as the force applied by or on the driving device 806A. In an example, the processor 802 may receive force information that indicates the impact force detected by the sensor 808, such as from the sensor 808. The processor 802 may determine that a cumulative force limit has been reached, such as based at least on the force information. The cumulative force limit may be determined based on stored force information from previous force detection from the sensor 808. The cumulative force limit may include a limit on a total force applied (e.g., a summation of total force applied), a number of impact forces performed (e.g., a raw number of strikes or rasps), a combination, or both. When the driving device 806A applies force with the broach 816, the cumulative force limit may include a weighting factor for stored imparted forces based on a size of the broach 816 or sizes of previous broaches. For example, an impact force may be multiplied by a weighting factor based on the size of a broach or a surface area of a striking area of a broach. In an example, the different sized broaches may apply different forces.

The processor 802 may determine feedback or feedback conditions, and communicate the feedback via an output device, and output via the output device to a surgeon controlling the driving device 806A, such as feedback indicating that the cumulative force limit has been reached. The cumulative force limit may be a limit below a threshold, wherein the threshold represents a maximum force, maximum number of impacts, a weighted maximum force, or the like. For example, the cumulative force limit may be a limit below a cumulative force (e.g., including a factor of safety) that may cause or will cause damage to a bone, implant, or surgical device. In this example, the feedback that the cumulative force limit has been reached may allow a surgeon to stop applying force using the driving device 806A, which may prevent impact damage to the bone or implant, or may improve a postsurgical outcome. The postsurgical outcome may be improved by limiting the force applied by the driving device 806A to a bone or implant. In an example, the feedback may include an audible alert, haptic feedback, a visual alert, a non-contact indication or the like.

In an example, data may be collected from the driving device 806A or the sensor 808. For example, a number of impacts, a peak impact force, an average force, metadata about the force, or the like may be stored, for example, in a database. The collected data may be used to track long-term outcomes, patient-specific outcomes, or the like. In an example, the collected data may be used to track post-operative pain, track post-operative success, such as, did the surgery fail, was a reopen necessary after a number of years, such as 10 years, etc. In an example, machine learning techniques may be used to track and improve future outcomes by adjusting a minimum or maximum force or a cumulative force. In an example, the collected data may be used to adjust a procedure, such as in a non-cement procedure, which may be more fragile than cement procedures. In an example, the feedback may be provided on a surgical drape within a field of view of the surgeon.

Figure 8B:
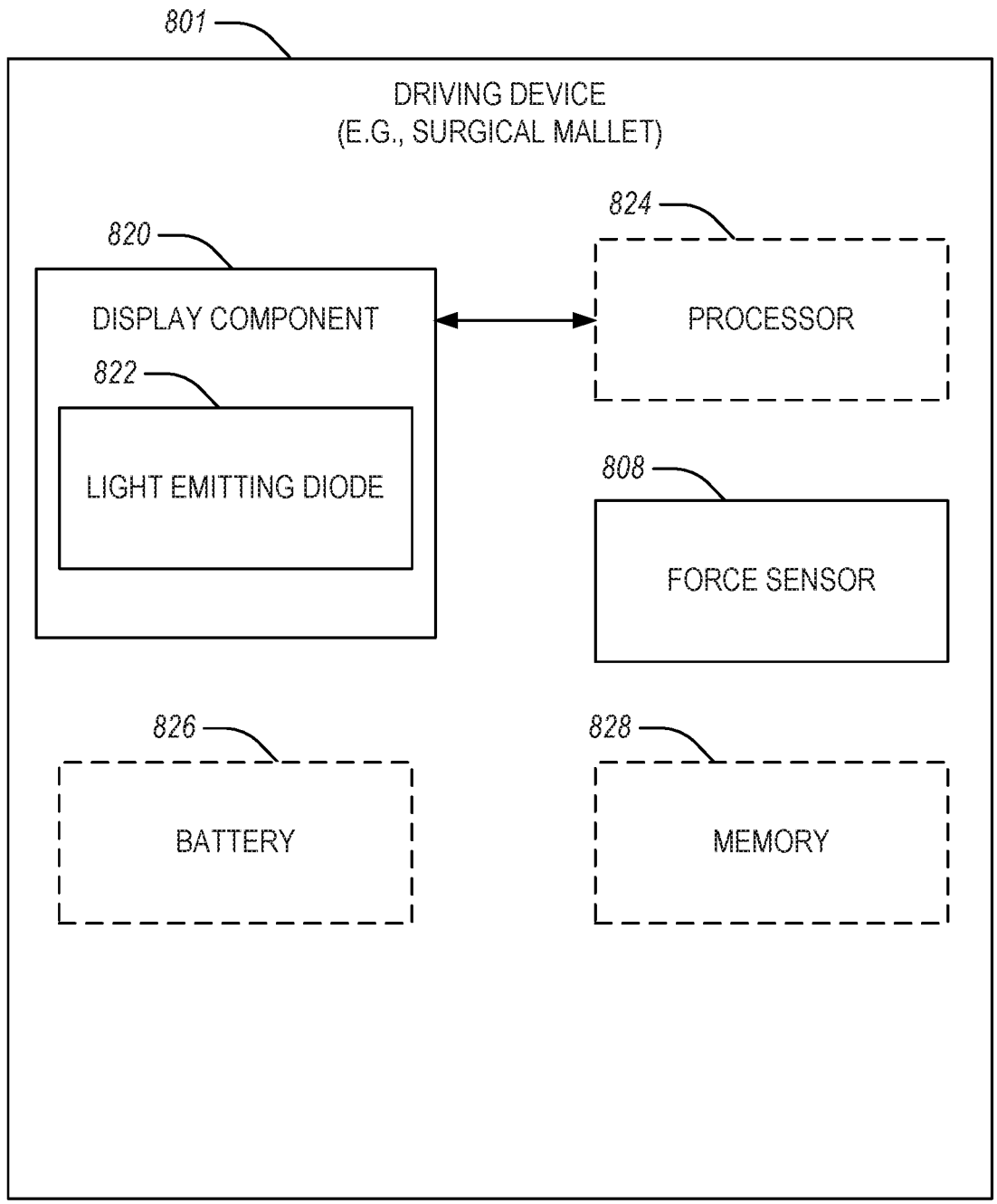
FIG. 8B illustrates an example system for displaying an impact force of a driving device used, for example, to seat an implant in accordance with some embodiments.

FIG. 8B illustrates an example system 800B for displaying an impact force of a driving device used, for example, to seat an implant in accordance with some embodiments. The system 800B includes a driving device 806B, such as a surgical mallet. The driving device 806B includes a display component 820 including at least one light emitting diode 822. The driving device 806B includes the sensor 808 (e.g., an accelerometer, pressure sensor, microphone, ultrasonic transceiver, a piezoelectric sensor, a resistive force sensor, a capacitive force sensor, another force sensor, or the like). The driving device 806B may include a processor 824, a battery 826, or memory 828.

The driving device 806B includes a shaft connected to a striking head on a distal end of the driving device the shaft including a force sensor to detect an impact force exerted by the striking head. The force sensor may include a force ring, such as within the surgical mallet adjacent to the striking head, which is compressed by the impact force. The shaft may include the display component 820 including the LED 822 to display a first visual indication of the impact force on the striking head.

The driving device 806B may include a graspable handle component or a removable component, which may be configured to insert into the graspable handle component. In an example, the removable component includes a rotational knob, a push button, or a switch to activate or deactivate the LED 822. In another example, the LED 822 may be affixed to a portion of the removable component or may be visible through the display component 820 of the shaft. In yet another example, the removable component may include a selectable mechanism to adjust the force range for the first visual indication, such as according to an object being struck by the striking head.

In an example, the LED 822 may include a red light emitting diode to indicate that the impact force exceeds a force range, a green light emitting diode to indicate that the impact force falls within the force range, or a blue or yellow light emitting diode to indicate that the impact force falls below the force range. The red light emitting diode may indicate potential damage to an implant. The blue or the yellow light emitting diode may indicate an insufficient force to seat the implant. In an example, the LED 822 may be located on the shaft of the surgical mallet.

In an example, the removable component, the graspable handle component, or another component of the driving device may include a battery housing to house the battery. The battery 826 may be used to power the processor 824, the sensor 808, or the LED 822.

The memory 828 may store instructions, which when executed by the processor 824, cause the processor to perform operations described herein. The processor 824 may determine whether the impact force exceeded a first threshold. The display component 820 may display the first visual indication of the impact force in response to the processor 824 determining that the impact force exceeded the first threshold. In an example, in response to the processor 824 determining that the impact force fell below the first threshold, the processor 824 may to determine whether the impact force exceeded a second threshold. In another example, in response to the processor 824 determining that the impact force exceeded the second threshold, the display component 820 may display a second visual indication of the impact force. In yet another example, in response to the processor 824 determining that the impact force fell below the second threshold, the display component 820 may display a third visual indication of the impact force. In an example, the second visual indication may correspond to an impact force within a selected range of force. The third visual indication may correspond to an impact force that is of insufficient force to seat an implant.

The techniques discussed above in reference to the impact driver (FIGS. 1A-2) can be similarly applied to the systems 800A and 800B. The system components discussed in reference to systems 800A and 800B can include similar circuity and LED lighting to provide similar feedback to a surgeon utilizing these devices.

Figure 9:
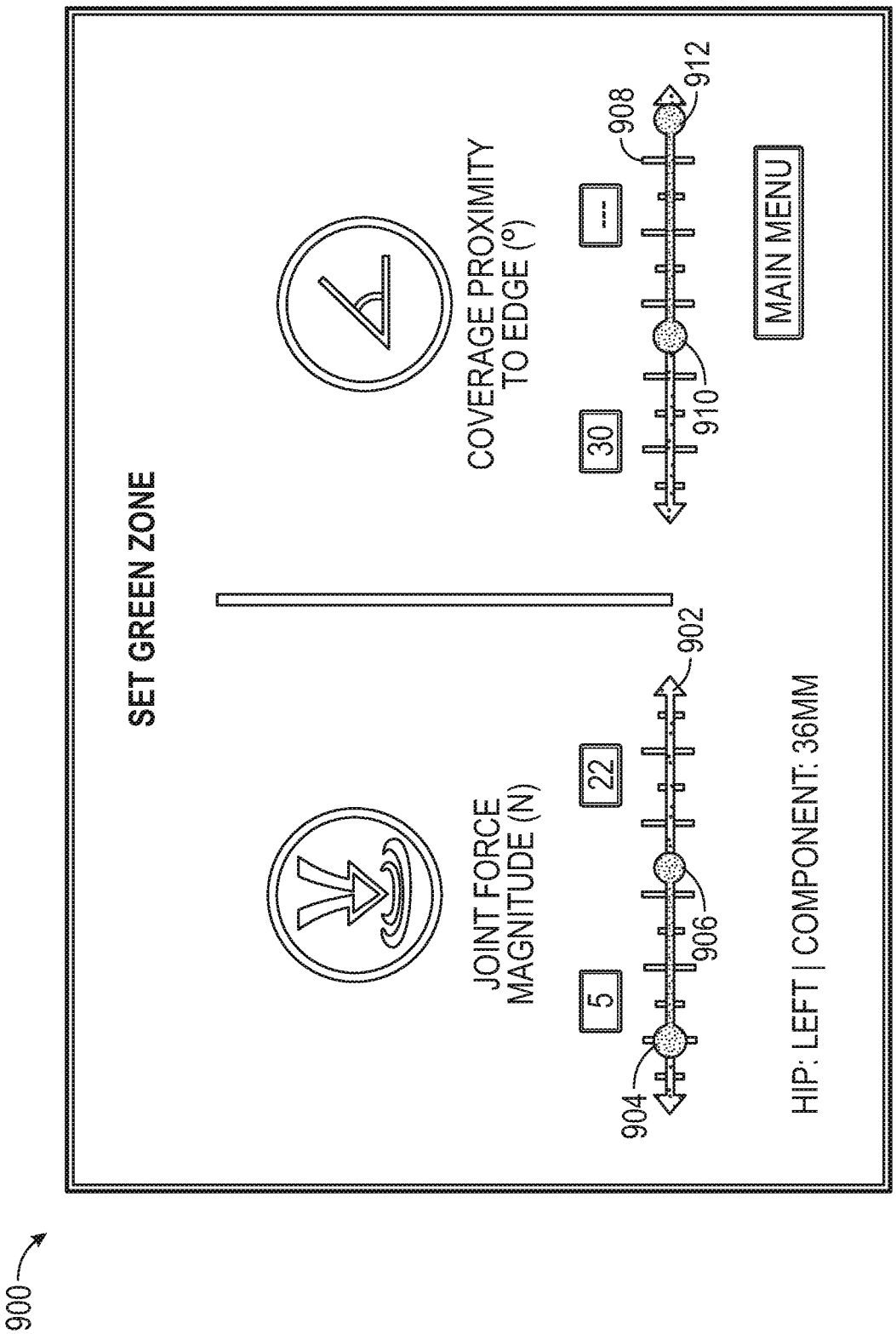
FIG. 9 illustrates a user interface for establishing joint force and proximity angle limits in accordance with some embodiments.

FIG. 9 illustrates a user interface 900 for establishing joint force and proximity angle limits in accordance with some embodiments. The user interface 900 may be used in conjunction with a driving device, such as the driving device 104 of FIGS. 1A-1C, the broaching device 300 of FIG. 3, the ball driver device 400 of FIG. 4, the driving device 500 of FIG. 5, or the like. The user interface 900 may supply information in addition to lighting components of or attached to one of the driving devices described above. For example, a surgeon may detect that a force is too great or is insufficient using the driving device 104 as a qualitative representation in a light. To obtain additional information about the force imparted, the surgeon may check the user interface 900. In an example, the user interface 900 may be monitored by an assistant, who may tell the surgeon the additional information such that the surgeon may remain focused on a procedure without needing to look away. For example, the surgeon may use one of the various driving devices described herein to be alerted to a qualitative indication of force impacted, and the assistant may tell the surgeon quantitative details when needed (e.g., when the surgeon sees the qualitative indication, the surgeon may ask for additional details, but may otherwise remain focused on the procedure). When the surgeon sees from the qualitative indication that the force is within a specified range, the surgeon may continue the procedure without needing to consult the user interface 900 or ask for additional information.

The user interface 900 includes a joint force magnitude scale 902 and a coverage proximity to edge scale 908. The joint force magnitude scale 902 includes a lower slider 904 and an upper slider 906 for selecting a joint force magnitude minimum and maximum, respectively. The coverage proximity to edge scale 908 includes a lower slider 910 and an upper slider 912 for selecting a coverage proximity angle minimum and maximum, respectively.

The user interface 900 allows a user to set the joint force magnitude limits (low and high) and the lower limit of the angle between the liner rim and the central force axis (e.g., "coverage"). In an example, the user interface 900 may allow the user to input basic information about the case or pre-operative planning requirements. This input may be used, along with the limits and the data received from sensors intraoperatively to create a personalized postoperative care plan. The data and input may be used in a feedback process, along with postoperative outcomes, to improve the functioning of a system for preventing damage to an implant component, a bone, or soft tissue caused by a driving device. In another example, limits may be recommended to the user on the user interface 900, such as machine learned limits from past data, which may, for example, take into account individual patient information.

Figure 10:
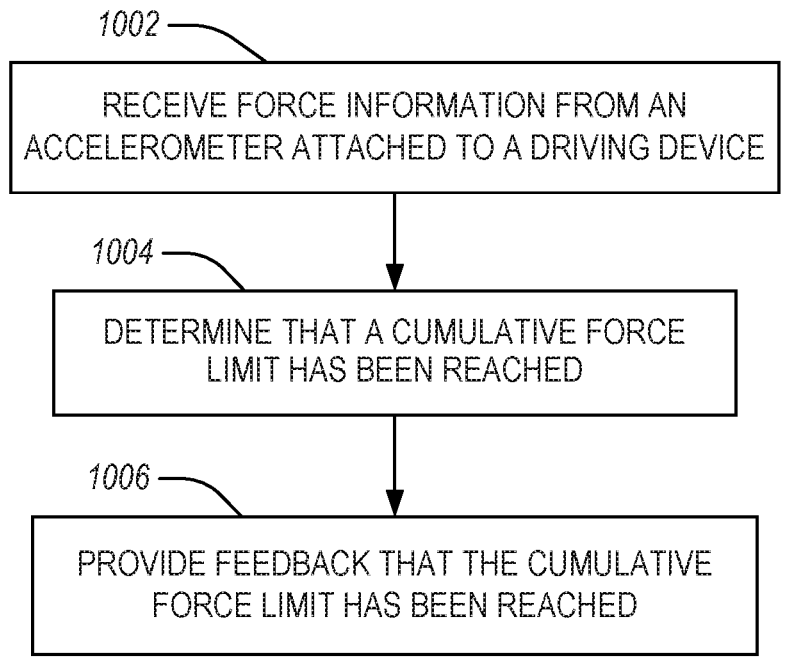
FIG. 10 illustrates a flowchart showing a technique for preventing damage to an implant component, a bone, or soft tissue during surgery in accordance with some embodiments.

FIG. 10 illustrates a flowchart showing a technique 1000 for preventing damage to an implant component, a bone, or soft tissue during surgery in accordance with some embodiments. The technique 1000 includes an operation 1002 to receive force information from an accelerometer, a piezoelectric sensor, a resistive force sensor, a capacitive force sensor, etc. attached to a driving device. Any of the surgical devices discussed above can include circuity and sensors to provide the for information utilized within technique 1000. The operation 1002 may include detecting, using an accelerometer or other force sensor of the driving device, an impact force exerted by the driving device. The force information may include information that indicates the impact force detected by the accelerometer. The impact force exerted by the driving device may include a broaching, a rasping, a chiseling, a seating, or other type of force. The impact force may include a force exerted by the driving device on a bone or an implant.

The technique 1000 includes an operation 1004 to determine that a cumulative force limit has been reached, such as by using the force information. The cumulative force limit may include a number of impact forces (e.g., a number of strikes) or a total force exerted (e.g., a total force over a period of time). The technique 1000 includes an operation 1006 to provide feedback that the cumulative force limit has been reached. In an example, the providing the feedback may include providing an audible alert, haptic feedback, a visual alert, a non-contact indication or the like. In another example, providing feedback may include wirelessly transmitting an indication that the cumulative force limit has been reached, such as from the driving device to a display (e.g., a remote display). The display may be used to provide a visual alert.

Figure 11:
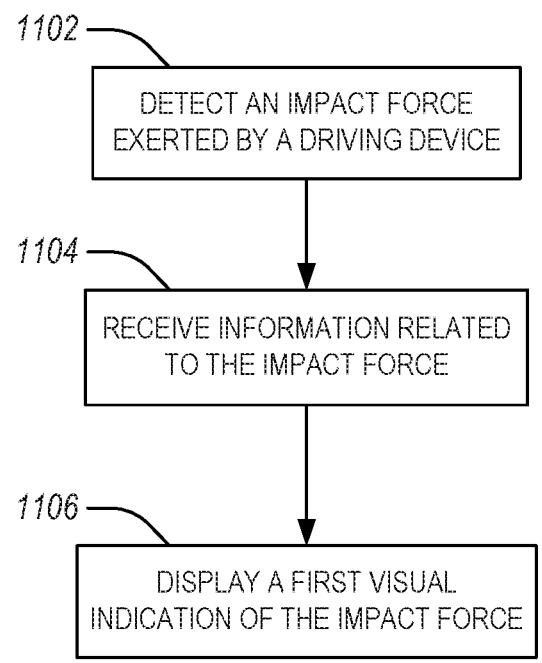
FIG. 11 illustrates a flow chart showing a technique for presenting visual feedback, such as of impact forces, at a driving device in accordance with some embodiments.

FIG. 11 illustrates a flow chart showing a technique 1100 for presenting visual feedback, such as of impact forces, at a driving device in accordance with some embodiments. In an example, the driving device may be a surgical mallet. The surgical mallet may strike an implant to seat the implant. The technique 1100 includes an operation 1102 to detect, such as by using a sensor of a driving device, an impact force exerted by a striking head of the driving device. For example, the sensor may include a force sensor such as a force ring that is compressed by the impact force. The technique 1100 includes an operation 1104 to receive, for example at a processor, information related to the impact force on the striking head of the driving device.

The technique 1100 includes an operation 1106 to display, such as by using at least one light emitting diode (LED) on a component of the driving device, a first visual indication of the impact force, such as in response to receiving the information. In an example, the at least one LED may include a red LED, such as to indicate that the impact force exceeds a force range, a green LED, such as to indicate that the impact force falls within the force range, or a blue or yellow LED, such as to indicate that the impact force falls below the force range. In an example, the red LED may indicate potential damage to an implant, such as from the impact force. The blue LED or the yellow LED may indicate an insufficient force to seat the implant. The green LED may indicate an appropriate force that will seat the implant without causing damage to the implant. The LED may be located on a handle component of the driving device. In an example, the LED may be located on a removable component insertable into the driving device. The removable component may include a rotational knob, a push button, or a switch to activate or deactivate the LED. The removable component may include a selectable mechanism to adjust a force range for the first visual indication according to an object being struck by the striking head.

The technique 1100 may include an optional operation to determine, such as by using a processor, whether the impact force exceeded a first threshold. Displaying the first visual indication of the impact force may include displaying the first visual indication in response to determining that the impact force exceeded the first threshold. The optional operation may include, in response to determining that the impact force fell below the first threshold, determining whether the impact force exceeded a second threshold. In an example, in response to determining that the impact force exceeded the second threshold, the technique 1100 may include displaying, using the at least one light emitting diode, a second visual indication. In an example, in response to determining that the impact force fell below the second threshold, the technique 1100 may include displaying, using the at least one light emitting diode, a third visual indication. The second visual indication may correspond to an impact force within a selected range of force. The third visual indication may correspond to an impact force that is of insufficient force to seat an implant. The first or second thresholds may be set according to patient parameters (e.g., using patient supplied information, preoperative imaging, bone density, soft tissue information, age of the patient, or the like). For example, a first patient may require more force to seat an implant than a second patient, so an acceptable force range (e.g., between the first and second thresholds) may be higher for the first patient than the second.

Figure 12:
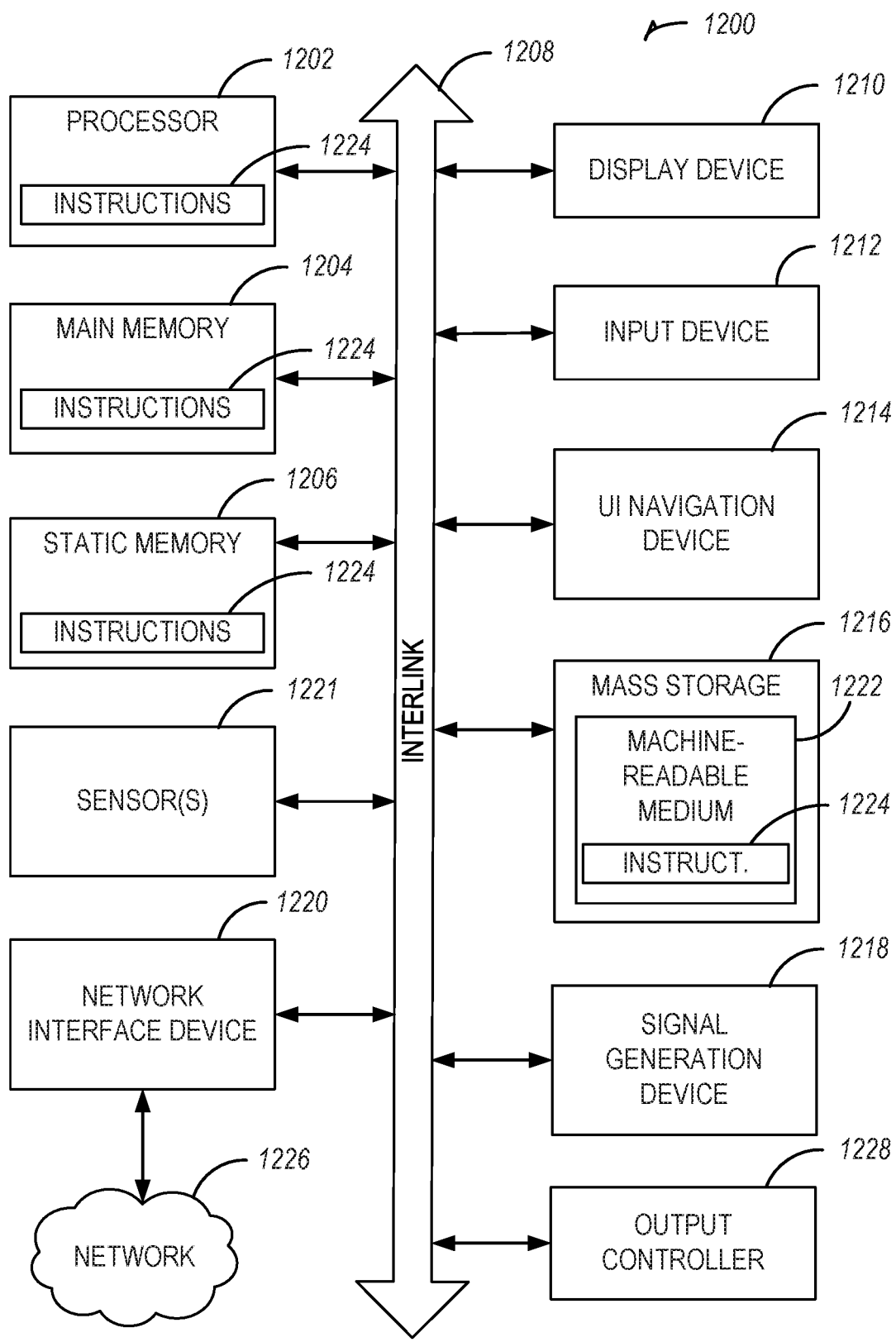
FIG. 12 illustrates generally an example of a block diagram of a machine upon which any one or more of the techniques discussed herein may perform in accordance with some embodiments.

FIG. 12 illustrates generally an example of a block diagram of a machine 1200 upon which any one or more of the techniques (e.g., methodologies) discussed herein may perform in accordance with some embodiments. In alternative embodiments, the machine 1200 may operate as a standalone device or may be connected (e.g., networked) to other machines. In a networked deployment, the machine 1200 may operate in the capacity of a server machine, a client machine, or both in server-client network environments. The machine 1200 may be a personal computer (PC), a tablet PC, a personal digital assistant (PDA), a mobile telephone, a web appliance, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate on, logic or a number of components, modules, or like mechanisms. Such mechanisms are tangible entities (e.g., hardware) capable of performing specified operations when operating. In an example, the hardware may be specifically configured to carry out a specific operation (e.g., hardwired). In an example, the hardware may include configurable execution units (e.g., transistors, circuits, etc.) and a computer readable medium containing instructions, where the instructions configure the execution units to carry out a specific operation when in operation. The configuring may occur under the direction of the executions units or a loading mechanism. Accordingly, the execution units are communicatively coupled to the computer readable medium when the device is operating. For example, under operation, the execution units may be configured by a first set of instructions to implement a first set of features at one point in time and reconfigured by a second set of instructions to implement a second set of features.

Machine (e.g., computer system) 1200 may include a hardware processor 1202 (e.g., a central processing unit (CPU), a graphics processing unit (GPU), a hardware processor core, or any combination thereof), a main memory 1204 and a static memory 1206, some or all of which may communicate with each other via an interlink (e.g., bus) 1208. The machine 1200 may further include a display unit 1210, an alphanumeric input device 1212 (e.g., a keyboard), and a user interface (UI) navigation device 1214 (e.g., a mouse). In an example, the display unit 1210, alphanumeric input device 1212 and UI navigation device 1214 may be a touch screen display. The machine 1200 may additionally include a storage device (e.g., drive unit) 1216, a signal generation device 1218 (e.g., a speaker), a network interface device 1220, and one or more sensors 1221, such as a global positioning system (GPS) sensor, compass, accelerometer, a piezoelectric sensor, a resistive force sensor, a capacitive force sensor, or other sensor. The machine 1200 may include an output controller 1228, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The storage device 1216 may include a machine readable medium 1222 that is non-transitory on which is stored one or more sets of data structures or instructions 1224 (e.g., software) embodying or utilized by any one or more of the techniques or functions described herein. The instructions 1224 may also reside, completely or at least partially, within the main memory 1204, within static memory 1206, or within the hardware processor 1202 during execution thereof by the machine 1200. In an example, one or any combination of the hardware processor 1202, the main memory 1204, the static memory 1206, or the storage device 1216 may constitute machine readable media.

While the machine readable medium 1222 is illustrated as a single medium, the term "machine readable medium" may include a single medium or multiple media (e.g., a centralized or distributed database, and/or associated caches and servers) configured to store the one or more instructions 1224.

The term "machine readable medium" may include any medium that is capable of storing, encoding, or carrying instructions for execution by the machine 1200 and that cause the machine 1200 to perform any one or more of the techniques of the present disclosure, or that is capable of storing, encoding or carrying data structures used by or associated with such instructions. Non-limiting machine readable medium examples may include solid-state memories, and optical and magnetic media. Specific examples of machine readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 1224 may further be transmitted or received over a communications network 1226 using a transmission medium via the network interface device 1220 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, as the personal area network family of standards known as Bluetooth® that are promulgated by the Bluetooth Special Interest Group, peer-to-peer (P2P) networks, among others. In an example, the network interface device 1220 may include one or more physical jacks (e.g., Ethernet, coaxial, or phone jacks) or one or more antennas to connect to the communications network 1226. In an example, the network interface device 1220 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 1200, and includes digital or analog communications signals or other intangible medium to facilitate communication of such software.

VARIOUS NOTES & EXAMPLES

Each of these non-limiting examples may stand on its own, or may be combined in various permutations or combinations with one or more of the other examples.

Example 1 is a method comprising: detecting, using a force sensor disposed within a striking component attached to a driving device, an impact force exerted by the striking component; outputting a voltage from the force sensor to circuitry controlling a lighting component configured to illuminate at least a portion of the striking component; and displaying, using lighting component, a first visual indication of the impact force based on the output voltage.

In Example 2, the subject matter of Example 1 includes, wherein when the impact force falls below a first threshold, outputting the voltage causes the lighting component to display a first color light, wherein when the impact force exceeds a second threshold, outputting the voltage causes the lighting component to display a second color light, and wherein when the impact force falls between the first and second thresholds, outputting the voltage causes the lighting component to display a third color light.

In Example 3, the subject matter of Example 2 includes, wherein the first color light is blue, the second color light is red, and the third color light is green.

In Example 4, the subject matter of Example 3 includes, wherein the red color light indicates potential damage to an implant and the blue color light indicates an insufficient force to seat the implant.

In Example 5, the subject matter of Examples 2-4 includes, wherein the first and second thresholds are predetermined.

In Example 6, the subject matter of Examples 1-5 includes, wherein the impact force is exerted by the striking component on a target object, the target object including one of a bone of a patient, an implant, a trial, or a test object.

In Example 7, the subject matter of Examples 1-6 includes, causing the striking component to be detached from the driving device.

In Example 8, the subject matter of Examples 1-7 includes, wherein detecting the impact force includes using a force ring within the striking component that is compressed by the impact force to determine the impact force.

In Example 9, the subject matter of Examples 1-8 includes, wherein detecting the impact force includes using a piezo-electric sensor within the striking component to determine the impact force.

In Example 10, the subject matter of Examples 1-9 includes, wherein the driving device is a surgical mallet.

Example 11 is a striking component coupled to a driving device for delivering an implant during a surgical procedure, the striking component comprising: a force sensor disposed within the striking component to: detect an impact force exerted by the striking component; output a voltage corresponding to the impact force; and circuitry to: control a lighting component using the output voltage to illuminate at least a portion of the striking component; and display, using the lighting component, a first visual indication of the impact force based on the output voltage corresponding to the impact force.

In Example 12, the subject matter of Example 11 includes, wherein when the impact force falls below a first threshold, the output voltage causes the lighting component to display a first color light, wherein when the impact force exceeds a second threshold, the output voltage causes the lighting component to display a second color light, and wherein when the impact force falls between the first and second thresholds, the output voltage causes the lighting component to display a third color light.

In Example 13, the subject matter of Example 12 includes, wherein the first color light is blue, the second color light is red, and the third color light is green.

In Example 14, the subject matter of Example 13 includes, wherein the red color light indicates potential damage to an implant and the blue color light diode indicates an insufficient force to seat the implant.

In Example 15, the subject matter of Examples 12-14 includes, wherein the first and second thresholds are predetermined.

In Example 16, the subject matter of Examples 11-15 includes, wherein the impact force is exerted by the striking component on a target object, the target object including one of a bone of a patient, an implant, a trial, or a test object.

In Example 17, the subject matter of Examples 11-16 includes, wherein the striking component further comprises a mechanism to cause the striking component to be detached from the driving device.

In Example 18, the subject matter of Examples 11-17 includes, wherein the force sensor is a force ring within the striking component that is compressed by the impact force to determine the impact force.

In Example 19, the subject matter of Examples 11-18 includes, wherein the force sensor is a piezo-electric sensor within the striking component.

In Example 20, the subject matter of Examples 11-19 includes, wherein the striking component further includes a battery to power the circuitry and the lighting component.

Example 21 is at least one machine-readable medium including instructions for presenting visual feedback, which when executed by a striking component coupled to a driving device, cause the striking component to: detect, using a force sensor disposed within a striking component attached to a driving device, an impact force exerted by the striking component; output a voltage from the force sensor to circuitry controlling a lighting component configured to illuminate at least a portion of the striking component; and display, using lighting component, a first visual indication of the impact force based on the output voltage.

In Example 22, the subject matter of Example 21 includes, wherein when the impact force falls below a first threshold, the output voltage causes the lighting component to display a first color light, wherein when the impact force exceeds a second threshold, the output voltage causes the lighting component to display a second color light, and wherein when the impact force falls between the first and second thresholds, the output voltage causes the lighting component to display a third color light.

In Example 23, the subject matter of Example 22 includes, wherein the first color light is blue, the second color light is red, and the third color light is green.

In Example 24, the subject matter of Example 23 includes, wherein the red light emitting diode indicates potential damage to an implant and the blue light emitting diode indicates an insufficient force to seat the implant.

In Example 25, the subject matter of Examples 22-24 includes, wherein the first and second thresholds are predetermined.

In Example 26, the subject matter of Examples 21-25 includes, wherein the impact force is exerted by the striking component on a target object, the target object including one of a bone of a patient, an implant, a trial, or a test object.

In Example 27, the subject matter of Examples 21-26 includes, instructions to cause the striking component to be detached from the driving device.

In Example 28, the subject matter of Examples 21-27 includes, wherein the instructions to detect the impact force include instructions to use a force ring within the striking component that is compressed by the impact force to determine the impact force.

In Example 29, the subject matter of Examples 21-28 includes, wherein the instructions to detect the impact force include instructions to use a piezo-electric sensor within the striking component to determine the impact force.

Example 30 is a method comprising: detecting, using a force sensor disposed within a driving device, an impact force exerted by a striking head of the driving device; receiving, at a processor within the driving device, information related to the impact force on the striking head of the driving device; and displaying, using at least one light emitting diode on a display component of the driving device, a first visual indication of the impact force in response to receiving the information.

In Example 31, the subject matter of Example 30 includes, determining, using the processor, whether the impact force exceeded a first threshold, and wherein displaying the first visual indication of the impact force includes displaying the first visual indication in response to determining that the impact force exceeded the first threshold.

In Example 32, the subject matter of Example 31 includes, in response to determining that the impact force fell below the first threshold, determining whether the impact force exceeded a second threshold; and in response to determining that the impact force exceeded the second threshold, displaying, using the at least one light emitting diode, a second visual indication; or in response to determining that the impact force fell below the second threshold, displaying, using the at least one light emitting diode, a third visual indication.

In Example 33, the subject matter of Example 32 includes, wherein the second visual indication corresponds to an impact force within a selected range of force and the third visual indication corresponds to an impact force that is of insufficient force to seat an implant.

In Example 34, the subject matter of Examples 30-33 includes, wherein displaying the first visual indication includes illuminating the at least one light emitting diode including a red light emitting diode to indicate that the impact force exceeds a force range, a green light emitting diode to indicate that the impact force falls within the force range, and a blue or yellow light emitting diode to indicate that the impact force falls below the force range.

In Example 35, the subject matter of Example 34 includes, wherein the red light emitting diode indicates potential damage to an implant and the blue or yellow light emitting diode indicates an insufficient force to seat the implant.

In Example 36, the subject matter of Examples 30-35 includes, wherein displaying the first visual indication includes illuminating the at least one light emitting diode located on a handle component of the driving device.

In Example 37, the subject matter of Examples 30-36 includes, wherein displaying the first visual indication includes illuminating the at least one light emitting diode located on a removable cartridge insertable into the driving device.

In Example 38, the subject matter of Example 37 includes, wherein the removable cartridge includes a rotational knob, a push button, or a switch to activate or deactivate the at least one light emitting diode.

In Example 39, the subject matter of Examples 37-38 includes, determining, using the processor, whether the impact force exceeded a first threshold; wherein displaying the first visual indication of the impact force includes displaying the first visual indication in response to determining that the impact force exceeded the first threshold; and wherein the first threshold is selected via a selectable mechanism within the removable cartridge, which adjusts a force range for the first visual indication according to an object being struck by the striking head.

In Example 40, the subject matter of Examples 30-39 includes, wherein receiving the information related to the impact force includes receiving force data from a force ring within the driving device that is compressed by the impact force.

In Example 41, the subject matter of Examples 30-40 includes, wherein the driving device is a surgical mallet.

Example 42 is a surgical mallet for delivering an implant during a surgical procedure, the surgical mallet comprising: a shaft connected to a striking head on a distal end of the surgical mallet; a force sensor disposed within the surgical mallet to detect an impact force exerted by the striking head; and a display component of the surgical mallet including at least one light emitting diode to display a first visual indication of the impact force on the striking head.

In Example 43, the subject matter of Example 42 includes, a graspable handle portion and a removable cartridge configured to insert into the graspable handle portion.

In Example 44, the subject matter of Example 43 includes, wherein the removable cartridge includes a rotational knob, a push button, or a switch to activate or deactivate the at least one light emitting diode.

In Example 45, the subject matter of Examples 43-44 includes, wherein the at least one light emitting diode is affixed to a portion of the removable cartridge and is visible through the display component of the shaft.

In Example 46, the subject matter of Examples 43-45 includes, wherein the removable cartridge includes a selectable mechanism to adjust the force range for the first visual indication according to an object being struck by the striking head.

In Example 47, the subject matter of Examples 42-46 includes, wherein the removable cartridge includes a battery to power the at least one light emitting diode.

In Example 48, the subject matter of Examples 42-47 includes, wherein the at least one light emitting diode includes a red light emitting diode to indicate that the impact force exceeds a force range, a green light emitting diode to indicate that the impact force falls within the force range, and a blue or yellow light emitting diode to indicate that the impact force falls below the force range.

In Example 49, the subject matter of Example 48 includes, wherein the red light emitting diode indicates potential damage to an implant and the blue or yellow light emitting diode indicates an insufficient force to seat the implant.

In Example 50, the subject matter of Examples 42-49 includes, wherein the at least one light emitting diode is located on the shaft of the surgical mallet.

In Example 51, the subject matter of Examples 42-50 includes, wherein the force sensor includes a force ring within the surgical mallet adjacent to the striking head that is compressed by the impact force.

In Example 52, the subject matter of Examples 42-51 includes, wherein the surgical mallet further comprises a processor to determine whether the impact force exceeded a first threshold, and wherein the display component is to display the first visual indication of the impact force in response to the processor determining that the impact force exceeded the first threshold.

In Example 53, the subject matter of Example 52 includes, wherein, in response to the processor determining that the impact force fell below the first threshold, the processor is further to determine whether the impact force exceeded a second threshold; and in response to the processor determining that the impact force exceeded the second threshold, the display component is to display a second visual indication of the impact force; or in response to the processor determining that the impact force fell below the second threshold, the display component is to display a third visual indication of the impact force.

In Example 54, the subject matter of Example 53 includes, wherein the second visual indication corresponds to an impact force within a selected range of force and the third visual indication corresponds to an impact force that is of insufficient force to seat an implant.

Example 55 is at least one machine-readable medium including instructions for presenting visual feedback, which when executed by an apparatus of a driving device, cause the apparatus of the driving device to: detect an impact force exerted by a striking head of the driving device; receive information related to the impact force on the striking head of the driving device from a force sensor of the driving device; and cause at least one light emitting diode on a display component of the driving device to display a first visual indication of the impact force in response to receiving the information.

In Example 56, the subject matter of Example 55 includes, instructions to determine whether the impact force exceeded a first threshold, and wherein the instructions to cause the at least one light emitting diode to display the first visual indication of the impact force include instructions to cause the at least one light emitting diode to display the first visual indication in response to determining that the impact force exceeded the first threshold.

In Example 57, the subject matter of Example 56 includes, instructions to determine, in response to determining that the impact force fell below the first threshold, whether the impact force exceeded a second threshold; and in response to determining that the impact force exceeded the second threshold, instructions to cause the at least one light emitting diode to display a second visual indication; or in response to determining that the impact force fell below the second threshold, instructions to cause the at least one light emitting diode to display a third visual indication.

In Example 58, the subject matter of Example 57 includes, wherein the second visual indication corresponds to an impact force within a selected range of force and the third visual indication corresponds to an impact force that is of insufficient force to seat an implant.

In Example 59, the subject matter of Examples 55-58 includes, wherein the instructions to display the first visual indication include instructions to illuminate the at least one light emitting diode including a red light emitting diode to indicate that the impact force exceeds a force range, a green light emitting diode to indicate that the impact force falls within the force range, or a blue or yellow light emitting diode to indicate that the impact force falls below the force range.

In Example 60, the subject matter of Example 59 includes, wherein the red light emitting diode indicates potential damage to an implant and the blue or yellow light emitting diode indicates an insufficient force to seat the implant.

In Example 61, the subject matter of Examples 55-60 includes, instructions to receive, from a control component of a removable cartridge insertable into the driving device, a control command for the driving device.

In Example 62, the subject matter of Example 61 includes, wherein the control command includes instructions to activate or deactivate the at least one light emitting diode.

In Example 63, the subject matter of Examples 61-62 includes, instructions to determine whether the impact force exceeded a first threshold; wherein the instructions to cause the at least one light emitting diode to display the first visual indication include instructions to cause the at least one light emitting diode to display the first visual indication in response to determining that the impact force exceeded the first threshold; and wherein the control command includes instructions to adjust a force range for the first visual indication according to an object being struck by the striking head.

In Example 64, the subject matter of Examples 55-63 includes, wherein the instructions to receive information related to the impact force include instructions to receive force data from a force ring within the driving device that is compressed by the impact force.

Example 65 is a system for preventing damage to an implant component, a bone, or soft tissue during surgery, the system comprising: a driving device to apply force; a force sensor to detect an impact force exerted by the driving device; and a processor to: receive force information that indicates the impact force detected by the force sensor; determine, based at least on the force information, that a cumulative force limit has been reached; and generate an output, including feedback to a surgeon controlling the driving device, the output indicating that the cumulative force limit has been reached.

In Example 66, the subject matter of Example 65 includes, wherein the driving device includes a broach.

In Example 67, the subject matter of Example 66 includes, a plurality of broaches of different sizes, the plurality of broaches used to apply different forces when connected to the driving device.

In Example 68, the subject matter of Example 67 includes, wherein to determine that the cumulative force limit has been reached, the processor is to determine that the cumulative force limit has been reached based at least on the different sizes of the plurality of broaches.

In Example 69, the subject matter of Examples 65-68 includes, wherein the force applied is a broaching, rasping, chiseling, or seating force.

In Example 70, the subject matter of Examples 65-69 includes, wherein the force sensor is embedded in a distal end of the driving device.

In Example 71, the subject matter of Examples 65-70 includes, wherein the impact force exerted by the driving device is exerted on the bone or the implant component.

In Example 72, the subject matter of Examples 65-71 includes, wherein the cumulative force limit indicates a limit on a number of impact forces or a limit on a total force exerted.

In Example 73, the subject matter of Examples 65-72 includes, wherein the feedback includes an audible alert, haptic feedback, or a visual alert.

In Example 74, the subject matter of Example 73 includes, wherein the driving device includes at least one of: a speaker to provide the audible alert, a haptic controller to provide the haptic feedback, or at least one light emitting diode to provide the visual alert.

In Example 75, the subject matter of Examples 65-74 includes, wherein the feedback is projected on a surgical drape within a field of view of the surgeon.

In Example 76, the subject matter of Examples 65-75 includes, a transceiver embedded in the driving device, the transceiver to wirelessly connect with a display, the display to provide a visual alert corresponding to the feedback.

Example 77 is a method for preventing damage to an implant component, a bone, or soft tissue during surgery, the method comprising: detecting, using a force sensor of a driving device, an impact force exerted by the driving device; receiving force information that indicates the impact force detected by the force sensor; determining, based at least on the force information, that a cumulative force limit has been reached; and generating an output, including feedback to a surgeon controlling the driving device, the output indicating that the cumulative force limit has been reached.

In Example 78, the subject matter of Example 77 includes, wherein the impact force exerted by the driving device is a broaching, rasping, chiseling, or seating force.

In Example 79, the subject matter of Examples 77-78 includes, wherein the cumulative force limit indicates a limit on a number of impact forces or a limit on a total force exerted.

In Example 80, the subject matter of Examples 77-79 includes, wherein generating the output includes causing an audible alert to be played, haptic feedback to be performed, or a visual alert to be displayed.

In Example 81, the subject matter of Examples 77-80 includes, wherein generating the output includes: wirelessly transmitting, to a display, an indication that the cumulative force limit has been reached; and displaying a visual alert on the display.

Example 82 is at least one machine-readable medium including instructions for receiving information, which when executed by a machine, cause the machine to: receive force information from a force sensor attached to a driving device, the force information including impact force measurement data; determine, based at least on the impact force measurement data, that a cumulative force limit has been reached; and generate an output, including feedback to a surgeon controlling the driving device, the output indicating that the cumulative force limit has been reached.

In Example 83, the subject matter of Example 82 includes, wherein the impact force measurement data includes data from a force exerted by the driving device on the bone or the implant component.

In Example 84, the subject matter of Examples 82-83 includes, wherein the instructions to generate the output include instructions to play an audible alert, cause haptic feedback, or display a visual alert.

Example 85 is at least one machine-readable medium including instructions that, when executed by processing circuitry, cause the processing circuitry to perform operations to implement of any of Examples 1-84.

Example 86 is an apparatus comprising means to implement of any of Examples 1-84.

Example 87 is a system to implement of any of Examples 1-84.

Example 88 is a method to implement of any of Examples 1-84.

Method examples described herein may be machine or computer-implemented at least in part. Some examples may include a computer-readable medium or machine-readable medium encoded with instructions operable to configure an electronic device to perform methods as described in the above examples. An implementation of such methods may include code, such as microcode, assembly language code, a higher-level language code, or the like. Such code may include computer readable instructions for performing various methods. The code may form portions of computer program products. Further, in an example, the code may be tangibly stored on one or more volatile, non-transitory, or non-volatile tangible computer-readable media, such as during execution or at other times. Examples of these tangible computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

What is claimed is:

1. A method comprising:
   detecting, using a force sensor located within a striking component secured to a driving device, an impact force exerted by the striking component on a target object;
   outputting a voltage from the force sensor to circuitry controlling a lighting component configured to illuminate at least a portion of the striking component;
   displaying, using the lighting component, a first visual indication of the impact force based on the output voltage; and
   causing the striking component to be detached from the driving device.

2. The method of claim 1, wherein when the impact force falls below a first threshold, outputting the voltage causes the lighting component to display a first color light, wherein when the impact force exceeds a second threshold, outputting the voltage causes the lighting component to display a second color light, and wherein when the impact force falls between the first and second thresholds, outputting the voltage causes the lighting component to display a third color light.

3. The method of claim 2, wherein displaying the second color light indicates potential damage to an implant and displaying the first color light indicates an insufficient force to seat the implant.

4. The method of claim 2, further comprising setting the first and second thresholds in reference to one or more patient parameters.

5. The method of claim 1, wherein the impact force is exerted by the striking component on a target object, the target object including one of a bone of a patient, an implant, a trial, or a test object.

6. The method of claim 1, wherein detecting the impact force includes using a force ring within the striking component, that is compressed by the impact force to determine the impact force.

7. The method of claim 1, wherein detecting the impact force includes using a piezo-electric sensor within the striking component to determine the impact force.

8. The method of claim 1, wherein the driving device is a surgical mallet.

9. A method comprising:
  detecting, using a force sensor located within a striking component connected to a driving device prior to impact, an impact force exerted on a target object by an impact surface of the striking component;
  outputting a voltage from the force sensor to circuitry controlling a lighting component configured to illuminate at least a portion of the striking component; and
  displaying, using the lighting component, a first visual indication of the impact force based on the output voltage; and
  causing the striking component to be detached from the driving device.

10. The method of claim 9, wherein detecting the impact force includes using a force ring within the striking component that is compressed by the impact force to determine the impact force.

11. The method of claim 9, wherein detecting the impact force includes using a piezoelectric sensor within the striking component to determine the impact force.

12. The method of claim 9, wherein the target object is one of a broach or a ball driver; and
  wherein detecting the impact force exerted includes detecting the impact force imparted to the broach or the ball driver by the striking component.

* * * * *

UNITED STATES PATENT AND TRADEMARK OFFICE
CERTIFICATE OF CORRECTION

PATENT NO. : 11,554,024 B2
APPLICATION NO. : 15/800988
DATED : January 17, 2023
INVENTOR(S) : Johannaber et al.

Page 1 of 1

It is certified that error appears in the above-identified patent and that said Letters Patent is hereby corrected as shown below:

In the Claims

In Column 24, Lines 60-61, in Claim 6, delete "component," and insert --component-- therefor In Column 25, Line 25, in Claim 12, delete "hall" and insert --ball-- therefor Signed and Sealed this
Fourth Day of March, 2025

Coke Morgan Stewart
*Acting Director of the United States Patent and Trademark Office*